United States Patent [19]

Takaya et al.

[11] 4,288,436

[45] Sep. 8, 1981

[54] 3,7-DISUBSTITUTED-3-CEPHEM-4-CARBOXYLIC ACID COMPOUNDS

[75] Inventors: Takao Takaya, Kawanishi; Masayoshi Murata, Mino, both of Japan

[73] Assignee: Fujisawa Pharmaceutical Co., Ltd., Osaka, Japan

[21] Appl. No.: 79,796

[22] Filed: Sep. 28, 1979

Related U.S. Application Data

[63] Continuation-in-part of Ser. No. 891,289, Mar. 29, 1978, abandoned.

[30] Foreign Application Priority Data

Apr. 13, 1977 [GB] United Kingdom ............... 15378/77
Jan. 23, 1978 [GB] United Kingdom ................ 2650/78

[51] Int. Cl.³ .................. A61K 31/545; C07D 501/56
[52] U.S. Cl. ..................... 424/246; 544/26; 544/27

[58] Field of Search ............. 544/27; 424/246

[56] References Cited

U.S. PATENT DOCUMENTS

| | | | |
|---|---|---|---|
| 4,098,888 | 7/1978 | Ochiai et al. | 424/246 |
| 4,100,346 | 7/1978 | Gottstein et al. | 544/27 |
| 4,165,373 | 8/1979 | Yamada et al. | 544/27 |
| 4,202,893 | 5/1980 | Heymes et al. | 544/27 |
| 4,220,644 | 9/1980 | Berges | 544/27 |

FOREIGN PATENT DOCUMENTS 2714880 10/1978 Fed. Rep. of Germany .

*Primary Examiner*—Paul M. Coughlan, Jr.
*Attorney, Agent, or Firm*—Dayton R. Stemple, Jr.

[57] ABSTRACT

Preparation of pharmaceutical composition comprising, treatment of human and animal diseases with, and compound of 3,7-disubstituted-3-cepham-4-carboxylic acid.

7 Claims, No Drawings

3,7-DISUBSTITUTED-3-CEPHEM-4-CARBOXYLIC ACID COMPOUNDS

This application is a continuation-in-part of co-pending application, Ser. No. 891,289, filed Mar. 29, 1978, now abandoned.

The present invention relates to new 3,7-disubstituted-3-cephem-4-carboxylic acid compounds and pharmaceutically acceptable salts thereof. More particularly, it relates to new 3,7-disubstituted-3-cephem-4-carboxylic acid compounds and pharmaceutically acceptable salts thereof which have antibacterial activities and to processes for the preparation thereof, to pharmaceutical composition comprising the same, and to a method of using the same therapeutically in the treatment of infectious diseases in human being and animals.

Accordingly, it is one object of the present invention to provide 3,7-disubstituted-3-cephem-4-carboxylic acid compounds and pharmaceutically acceptable salts thereof, which are highly active against a number of pathogenic bacteria.

Another object of the present invention is to provide processes for the preparation of 3,7-disubstituted-3-cephem-4-carboxylic acid compounds and pharmaceutically acceptable salts thereof.

A further object of the present invention is to provide pharmaceutical composition comprising, as active ingredients, said 3,7-disubstituted-3-cephem-4-carboxylic acid compounds and pharmaceutically acceptable salts thereof.

Still further object of the present invention is to provide a method for the treatment of infectious diseases caused by pathogenic bateria in human being and animals.

The object 3,7-disubstituted-3-cephem-4-carboxylic acid compounds are novel and can be represented by the following formula (I):

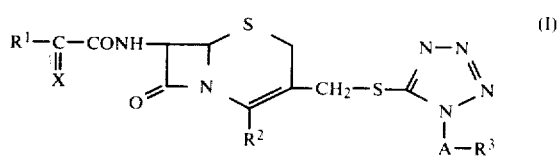

wherein
$R^1$ is S and N- containing heterocyclic group or S-containing 6-membered heterocyclic group, each of which may have suitable substituent(s), or an aryl having suitable substituent(s);
$R^2$ is carboxy or protected carboxy;
$R^3$ is carboxy or protected carboxy;
X is oxo, hydroxyimino, ar(lower)alkoxyimino, or saturated or unsaturated lower alkoxyimino; and
A is lower alkylene; provided that when $R^1$ is a group of the formula:

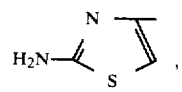

X is oxo, hydroxyimino, ar(lower)alkoxyimino, or saturated or unsaturated lower alkoxyimino having more than one carbon atom.

The object compounds of the present invention (I) are novel compounds and can be prepared by the Processes 1 to 3 as mentioned below.

Process 1

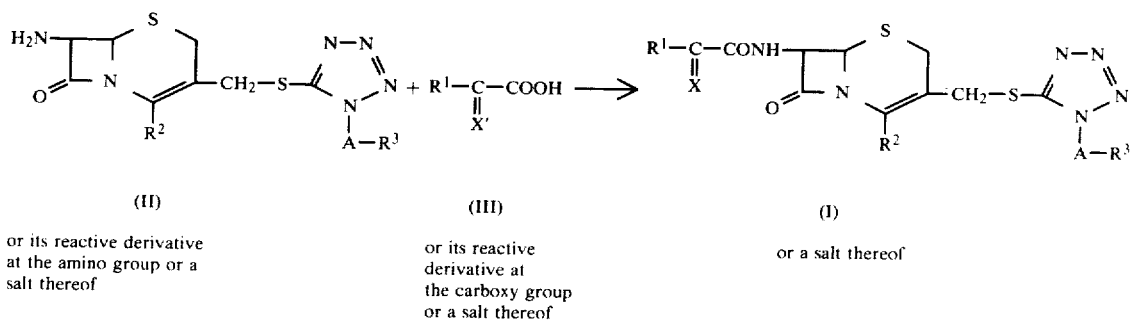

| (II) | (III) | (I) |
|---|---|---|
| or its reactive derivative at the amino group or a salt thereof | or its reactive derivative at the carboxy group or a salt thereof | or a salt thereof |

Process 2

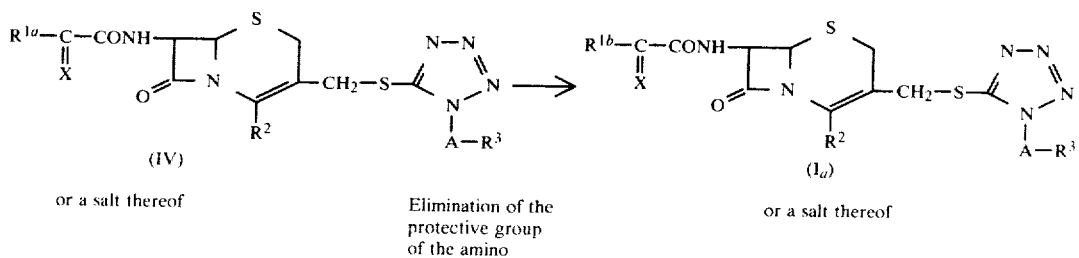

| (IV) | | (Iₐ) |
|---|---|---|
| or a salt thereof | Elimination of the protective group of the amino | or a salt thereof |

Process 3

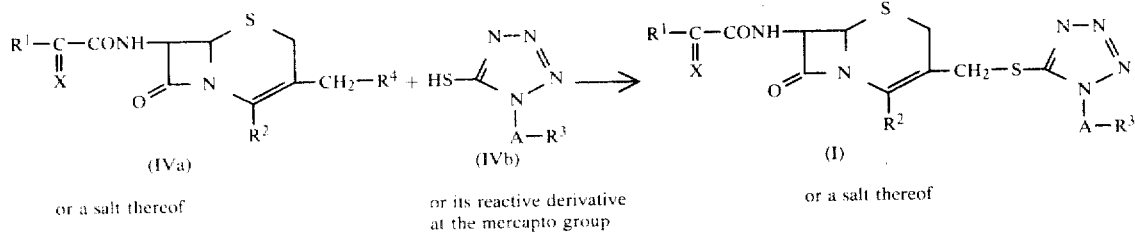

wherein
R[1], R[2], R[3], X and A are each as defined above;
X' is oxo, hydroxyimino, protected hydroxyimino, ar(lower)alkoxyimino, or saturated or unsaturated lower alkoxyimino;
R[1a] is S and N- containing heterocyclic group, S-containing 6-membered heterocyclic group or an aryl, each of which has protected amino;
R[1b] is S and N- containing heterocyclic group, S—containing 6-membered heterocyclic group or an aryl, each of which has amino; and
R[4] is a group which can be substituted by a group

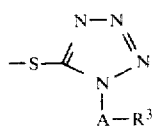

wherein R[3] and A are each as defined above; and provided that when R[1b] is a group of the formula:

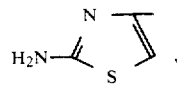

X is oxo, hydroxyimino, ar(lower)alkoxyimino, or saturated or unsaturated lower alkoxyimino having more than one carbon atom.

Among the starting compounds, some of the compound (III) is novel and can be prepared by the processes which are illustrated by the following scheme.

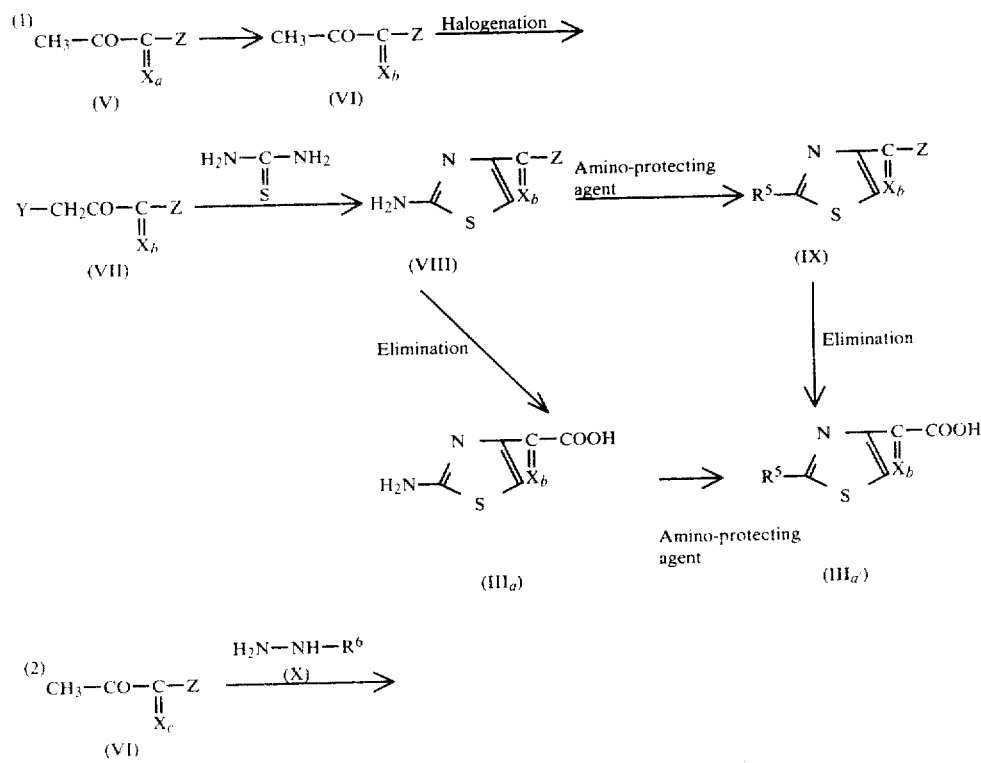

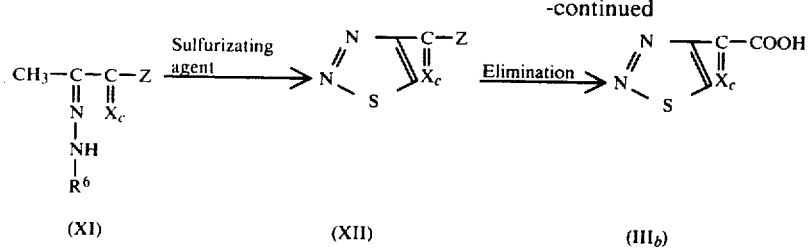

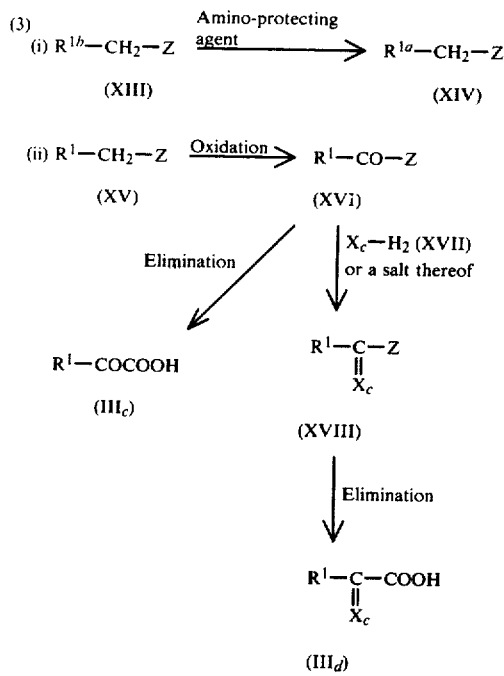

wherein
- $R^1$, $R^{1a}$ and $R^{1b}$ are each as defined above;
- $X_a$ is hydroxyimino;
- $X_b$ is ar(lower)alkoxyimino, or saturated or unsaturated lower alkoxyimino;
- Z is protected carboxy;
- Y is halogen;
- $R^5$ is protected amino;
- $X_c$ is hydroxyimino, ar(lower)alkoxyimino, or saturated or unsaturated lower alkoxyimino; and
- $R^6$ is protective group for amino.

The other starting compound (IV) is also novel and can be prepared by Processes 1 or 3 and the compound (IVa) can be prepared by reacting a compound of the formula:

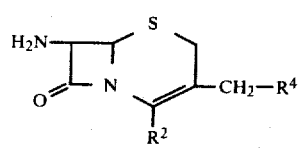

wherein $R^2$ and $R^4$ are each as defined above, with a compound of the formula:

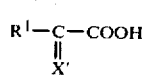 (III)

wherein $R^1$ and $X'$ are each as defined above, in a similar manner to that of Process 1.

In the object compound (I), in case that the symbol X means hydroxyimino, ar(lower)alkoxyimino, or saturated or unsaturated lower alkoxyimino, the partial structure thereof can be represented by the formula:

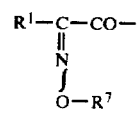

(wherein $R^7$ is hydrogen, ar(lower)alkyl, or saturated or unsaturated lower alkyl), and the above partial structure is to be understood to include both of the syn-geometrical structure of the formula:

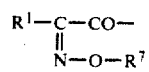

and the anti-geometrical structure of the formula:

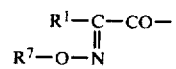

In this specification, with regard to all the compounds having hydroxyimino, protected hydroxyimino, ar(lower)alkoxyimino, or saturated or unsaturated lower alkoxyimino, the compounds having the geometrical partial structure shown by the formula

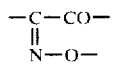

are referred to as "syn-isomer" and the compounds having the alternative one shown by the formula

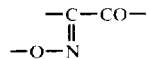

as "anti-isomer."

Suitable pharmaceutically acceptable salt of the object compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc., an organic salt, for example, an organic amine salt (e.g., trimethylamine salt, triethylamine salt, ethanolamine salt, diethanolamine salt, pyridine salt, picoline salt, dicyclohexylamine salt, N,N'-dibenzylethylenediamine salt, etc.) etc., an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention intend to include within the scope thereof are explained in details as follows.

The term "lower" is intended to mean 1 to 6 carbon atom(s), unless otherwise provided.

S and N- containing heterocyclic group means (3 to 8-membered) saturated (or unsaturated), monocyclic (or polycyclic) heterocyclic group containing at least one sulfur atom and one nitrogen atom.

And, suitable S and N- containing heterocyclic group may include saturated 3 to 8-membered (preferably 5 to 6-membered, more preferably 5-membered) heteromonocyclic group containing 1 to 2 sulfur atom(s) and 1 to 3 nitrogen atom(s), for example, thiazolyl (e.g., 1,2-thiazolyl or 1,3-thiazolyl), thiadiazolyl (e.g., 1,2,3-thiadiazolyl, 1,2,4-thiadiazolyl, 1,3,4-thiadiazolyl, 1,2,5-thiadiazolyl, etc.), etc.; saturated 3 to 8-membered (preferably 5 to 6 membered) heteromonocyclic group containing 1 to 2 sulfur atom(s) and 1 to 3 nitrogen atom(s), for example, thiazolidinyl, etc.; unsaturated condensed heterocyclic group containing 1 to 2 sulfur atom(s) and 1 to 3 nitrogen atom(s), for example, benzothiazolyl, benzothiadiazolyl, etc. and the like; in which said heterocyclic group may have 1 to 2 suitable substituent(s) such as amino; protected amino; lower alkyl (e.g., methyl, ethyl, propyl, isopropyl, butyl, isobutyl, pentyl, cyclopentyl, hexyl, cyclohexyl, etc.); hydroxy; aryl (e.g., phenyl, tolyl, etc.); halogen (e.g., chlorine, bromine, iodine or fluorine); or the like.

As to the S and N- containing heterocyclic group as mentioned above, the following points are to be noted. That is, in case that "S and N- containing heterocyclic group which may have suitable substituent(s)" for $R^1$ is specifically thiazolyl (e.g. 1,3-thiazolyl) group having amino or protected amino as a substituent in its molecule, the object compound (I) and the starting compound (III) include tautomeric isomers, which are caused by the specific behavior of the thiazole ring. That is, for example, said amino- or protected amino-1,3-thiazolyl group is represented by the formula:

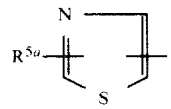

(wherein $R^{5a}$ is amino or protected amino), and in case that the group of the formula (A) takes the formula:

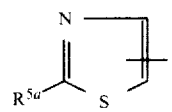

(wherein $R^{5a}$ is amino or protected amino), said group of the formula (A') can also be alternatively represented by its tautomeric formula:

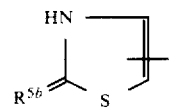

(wherein $R^{5b}$ is imino or protected imino). That is, both of the said groups of the formulae (A') and (A") are in the state of tautomeric equilibrium which can be represented by the following equilibrium:

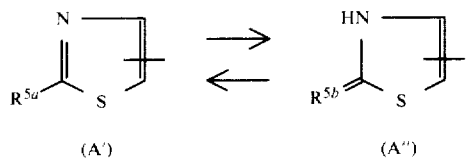

(wherein $R^{5a}$ and $R^{5b}$ are each as defined above).

These types of tautomerism between 2-aminothiazole compounds and 2-iminothiazoline compounds as stated above have been well known in the arts, and it is obvious to a person skilled in arts that both of the tautomeric isomers are equilibrated and lie in the reciprocally convertible state, and accordingly it is to be understood that such isomers are included within the same category of the compound per se. Accordingly, the both of the tautomeric forms of the object compounds (I) and (Ia), and the starting compounds (III), (IIIa), (IIIa'), (IIIc), (IIId), (IV), (IVa), (VIII), (IX), (XIII)-(XVI) and (XVIII) are clearly included within the scope of the present invention. In the present specification, the object and starting compounds including the group of such tautomeric isomers are represented by using one of the expressions therefor, i.e. 2-amino(or protected amino)-1,3-thiazolyl and the formula:

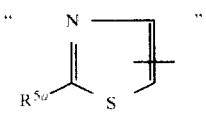

only for the convenient sake.

Suitable protected amino may include an acylamino and amino group substituted by a conventional protective group other than the acyl group such as ar(lower)alkyl (e.g., benzyl, trityl, etc.) or the like.

Suitable protected imino may include an acylimino and imino group substituted by a conventional protective group other than the acyl group such as aforesaid ar(lower)alkyl or the like.

Suitable acyl moiety in the terms "acylamino" and "acylimino" as mentioned above may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s);

lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc), preferably one having 3 to 6 carbon atoms;

lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.);

ar(lower)alkanoyl (e.g., phenylacetyl, phenylpropionyl, etc.); ar(lower)alkoxycarbonyl (e.g., benzyloxycarbonyl, phenethyloxycarbonyl, etc.); and the like.

The acyl moiety as stated above may have 1 to 3 suitable substituent(s) such as halogen (e.g., chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl etc.), aryl (e.g., phenyl, tolyl, etc.), or the like. Preferable examples of the acyl having said substituent(s) may be mono(or di or tri)halo(lower)alkanoyl (e.g., trifluoroacetyl, trichloroacetyl, dichloroacetyl, etc.) or the like.

S-containing 6-membered heterocyclic group means saturated or unsaturated 6-membered heterocyclic group containing at least one sulfur atom.

And, suitable S-containing 6-membered heterocyclic group may include unsaturated 6-membered heterocyclic group containing 1 to 2 sulfur atom(s), for example, dihydrodithiinyl, dithiinyl, etc.;

saturated 6-membered heterocyclic group containing 1 to 2 sulfur atom(s), for example, tetrahydrodithiinyl, etc.;

and the like, in which said S-containing 6-membered heterocyclic group may have 1 to 2 suitable substituent(s) as exemplified for S and N- containing heterocyclic group.

Suitable aryl may include phenyl, tolyl, xylyl, mesityl, cumenyl, naphthyl and the like, which has 1 to 2 suitable substituent(s) as exemplified for S and N- containing heterocyclic group.

Suitable protected carboxy may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.), wherein lower alkyl moiety may be preferably one having 1 to 4 carbon atom(s); lower alkenyl ester (e.g., vinyl ester, allyl ester etc.);

lower alkynyl ester (e.g., ethynyl ester, propynyl ester, etc.); mono(or di or tri)halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester etc.);

ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);

aryl ester which may have one or more suitable substituent(s) (e.g., phenyl ester, tolyl ester, tertiarybutylphenyl ester, xylyl ester, mesityl ester, cumenyl ester, etc.), and the like. Preferable example of protected carboxy may be lower alkoxycarbonyl (e.g., methoxycarbonyl, ethoxycarbonyl, propoxycarbonyl, butoxycarbonyl, t-butoxycarbonyl, t-pentyloxycarbonyl, hexyloxycarbonyl, etc.) having 2 to 7 carbon atoms, preferably one having 2 to 5 carbon atoms.

Suitable ar(lower)alkoxyimino may include one having 7 to 19 carbon atoms, such as benzyloxyimino, phenethyloxyimino, trityloxyimino, tolylmethoxyimino or the like.

Suitable saturated or unsaturated lower alkoxyimino may include lower alkoxyimino, lower alkenyloxyimino, lower alkynyloxyimino and the like.

Suitable lower alkoxyimino may include straight or branched one having 1 to 6 carbon atom(s), such as methoxyimino, ethoxyimino, propoxyimino, isopropoxyimino, butoxyimino, isobutoxyimino, t-butoxyimino, pentyloxyimino, hexyloxyimino, or the like, and cyclo(lower)alkoxyimino having 3 to 6 carbon atoms, such as cyclopropyloxyimino, cyclopentyloxyimino, cyclohexyloxyimino, or the like.

Suitable lower alkenyloxyimino may include straight or branched one having 2 to 6 carbon atoms, such as vinyloxyimino, allyloxyimino, isopropenyloxyimino, 1-propenyloxyimino, 2-butenyloxyimino, 3-pentenyloxyimino or the like, and preferably one having 2 to 4 carbon atoms.

Suitable lower alkynyloxyimino may include straight or branched one having 2 to 6 carbon atoms, such as ethynyloxyimino, 2-propynyloxyimino, 2-butynyloxyimino, 3-pentynyloxyimino, 3-hexynyloxyimino or the like, and preferably one having 2 to 4 carbon atoms.

Suitable lower alkylene may include straight or branched bivalent aliphatic hydrocarbon residue having 1 to 6 carbon atom(s), such as methylene, ethylene, methylethylene, propylene, trimethylene, 2-methyltrimethylene or the like, and preferably one having 1 to 4 carbon atom(s), more preferably one having 1 to 2 carbon atom(s).

Suitable group which can be substituted by a group

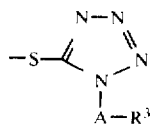

may include an acid residue such as halogen, azido, acyloxy or the like, wherein halogen and acyl moiety in "acyloxy" can be referred to the ones as exemplified in this specification.

Suitable protected hydroxyimino may include acyloxyimino in which acyl moiety can be referred to the acyl moiety as exemplified above.

Suitable halogen may include chlorine, bromine, fluorine and iodine.

Suitable protective group for amino may be referred to the ones exemplified as aforementioned acyl moiety.

Suitable ar(lower)alkyl and saturated or unsaturated lower alkyl for $R^7$ may be ar(lower)alkyl moiety in the ar(-lower)alkoxyimino and saturated or unsaturated lower alkoxyimino as mentioned above, respectively.

Among the examples of each of the groups of the object compounds as explained and illustrated above, the preferred examples thereof are more specifically illustrated as follows.

$R^1$ is thiazolyl (more preferably 1,3-thiazolyl) having amino or protected amino [more preferably lower alkanoylamino, halo(lower)alkanoylamino, lower alkoxycarbonylamino or ar(lower)alkylamino], thiadiazolyl (more preferably 1,2,3-thiadiazolyl), dihydrodithiinyl or aryl (more preferably phenyl) having hydroxy, amino or protected amino (more preferably lower alkanoylamino);

$R^2$ is carboxy;

$R^3$ is carboxy or lower alkoxycarbonyl;

X is oxo, hydroxyimino, ar(lower)alkoxyimino, lower alkoxyimino, lower alkenyloxyimino or lower alkynyloxyimino; and A is lower alkylene.

The various processes for preparing the object compounds of the present invention are explained in details in the following.

Process 1:

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include conventional reactive derivative used in amidation, for example, Schiff's base type imino or its tautomeric enamine type isomer formed by the reaction of the compound (II) with a carbonyl compound; a silyl derivative formed by the reaction of the compound (II) with a silyl compound such as bis(trimethylsilyl)acetamide, trimethylsilylacetamide or the like; a derivative formed by reaction of the compound (II) with phosphorus trichloride or phosgene, and the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, dimethylpyrazole, triazole or tetrazole; or an activated ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (III) to be used.

The salts of the compound (III) may be salts with an inorganic base such as an alkali metal salts (e.g., sodium or potassium salt), or an alkaline earth metal salt (e.g., calcium or magnesium salt), a salt with an organic base such as trimethylamine, triethylamine, pyridine, a salt with an acid (e.g., hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the compound (III) is used in free acid from or its salt form in the reaction, the reaction is preferably carried out in the presence of a conventional condensing agent such as N,N-dicyclohexylcarbodiimide; N-cyclohexyl-N'-morpholinoethylcarbodiimide; N-cyclohexyl-N'-(4-diethylaminocyclohexyl)carbodiimide; N,N-diethylcarbodiimide; N,N-diisopropylcarbodiimide; N-ethyl-N'-(3-dimethylaminopropyl)carbodiimide; N,N-carbonylbis(2-methylimidazole); pentamethyleneketene-N-cyclohexylimine; diphenylketene-N-cyclohexylimine; ethoxyacetylene; ethylene polyphosphate; isopropyl polyphosphate; diethyl phosphorochloridite; phosphorus oxychloride; phosphorus trichloride; thionyl chloride; oxalyl chloride; triphenylphosphine; N-ethyl-7-hydroxybenzisoxazolium fluoroborate; N-ethyl-5-phenylisoxazolium-3'-sulfonate; 1-(p-chlorobenzenesulfonyloxy)-6-chloro-1H-benzotriazole; so-called Vilsmeier reagent, for example, (chloromethylene)dimethylammonium chloride produced by the reaction of dimethylformamide with thionyl chloride or phosgene, a compound produced by the reaction of dimethylformamide with phosphorus oxychloride, etc., or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorphorine, N,N-di(-lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, it is to be noted that in case that the starting compound (III), wherein X' is hydroxyimino, protected hydroxyimino, ar(lower)alkoxyimino, or saturated or unsaturated lower alkoxyimino, is reacted with the compound (II) or its derivative at the amino group or a salt thereof in the presence of, for example, phosphorus pentachloride, thionyl chloride, etc., only anti-isomer of the object compound (I) or a mixture of the anti-isomer and syn-isomer thereof may be given as an object compound even if the syn-isomer of the compound (III) is used as a starting compound. It may be understood that the tendency of such isomerization in the reaction as mentioned above is due to the fact that the less stable syn-isomer tends to isomerize partially or wholly to the corresponding more stable anti-isomer in the course of the reaction, for example, in so-called activation step of the compound (III) so that more stable isomer, i.e. the anti-isomer of the object compound (I) is produced as the reaction product.

Accordingly, in order to obtain a syn-isomer of the object compound (I) selectively and in high yield, it is necessary to use a syn-isomer of the starting compound (III), and to conduct the reaction in the selected reaction condition. That is, a syn-isomer of the object compound (I) can be obtained selectively and in high yield by conducting the reaction of the compound (II) with a syn-isomer of the starting compound (III), for example, in the presence of a Vilsmeier reagent as mentioned above etc. and under around neutral condition.

Especially, in case that the starting compound (III) wherein $R^1$ is a group of the formula:

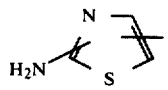

is used, a syn-isomer of the object compound (I) having free amino group on thiazolyl group for $R^1$ can be obtained selectively and in high yield by conducting the present reaction of the corresponding syn-isomer of the starting compound (III) with the compound (II), for example, in the presence of a Vilsmeier reagent produced by the reaction of dimethylformamide with phosphorus oxychloride and under around neutral condition. And, in this case, it is to be noted that particularly good results can be achieved by conducting the reaction in the presence of more than two molar equivalents of phosphorus oxychloride to each amount of the said syn-isomer of the starting compound (III) and dimethylformamide.

Further, in this case, it is to be also noted that good results can be achieved by conducting an activation step of the syn-isomer of the starting compound (III) in the presence of a silyl compound [e.g. bis(trimethylsilyl)acetamide, trimethylsilylacetamide, etc.] and the like.

In the present reaction, there may be obtained the resulting compound having protected hydroxyimino according to reaction conditions, a kind of protective group etc. In this case, the protective group is eliminated by conventional manners.

Process 2:

The object compound ($I_a$) or a salt thereof can be prepared by subjecting the compound (IV) or a salt thereof to elimination reaction of the protective group of the amino.

Suitable salt of the compound (IV) may include a metal salt, ammonium salt, an organic amine salt and the like as aforementioned.

The present elimination reaction is carried out in accordance with a conventional method such as hydrolysis; reduction; a method by reacting the compound (IV) wherein the pretective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g., t-pentyloxycarbonyl, etc.), alkanoyl (e.g., formyl, etc.), cycloalkoxycarbonyl, substituted or unsubstituted aralkoxycarboxyl (e.g., benzyloxycarbonyl, substituted benzyloxycarbonyl, etc.), substituted phenylthio, substituted aralkylidene, substituted alkylidene, substituted cycloalkylidene, ar(lower)alkyl (e.g., benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is an acid which can be easily removed from the reaction mixture by a conventional manner such as distillation under reduced pressure, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent, water or a mixture thereof. When trifluoroacetic acid is used, the elimination reaction may be preferably carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g., trifluoroacetyl, etc.) etc. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.) alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene5-or the like. The hydrolysis using a base is often carried out in water, a conventional organic solvent or a mixture thereof.

Among the protective group, the acyl group can be generally eliminated by hydrolysis as mentiond above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g., trichloroethoxycarbonyl etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g., sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present reaction includes, within its scope, the cases that the protected carboxy group for $R^2$ and/or $R^3$ is transformed into the free carboxy group, and/or ar(lower)alkoxyimino for X is transformed into hydroxyimino in the course of the elimination reaction as mentioned above or in the post-treatment of the reaction mixture or reaction product.

Process 3:

The object compound (I) or a salt thereof can be prepared by reacting the compound (IVa) or a salt thereof with the compound (IVb) or its reactive derivative at the mercapto group.

Suitable salt of the compound (IVa) can be referred to the ones exemplified for the compound (II).

Suitable reactive derivative at the mercapto group of the compound (IVb) may include a metal salt such as an alkali metal salt (e.g., sodium salt, potassium salt, etc.) or the like.

The present reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (IVa) or the compound (IVb) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature or under warming.

The reaction product of the aforementioned Processes 1 to 3 can be isolated from the reaction mixture by conventional methods.

In the aforementioned reactions and/or in the post treatment of the reactions of the present invention, the aforementioned tautomeric isomers may be occasionally transformed into the other tautomeric isomers and such case is also included in the scope of the present invention.

In case that the object compound (I) is obtained in a form of the free acid at 4 position and/or at the terminal position of the lower alkylene moiety attached to the tetrazolylthiomethyl group at 3 position and/or in case that the object compound (I) has free amino group, it may be optionally transformed into its pharmaceutically acceptable salt as aforementioned by a conventional method.

The object compound (I) and pharmaceutically acceptable salt thereof of the present invention are all novel compounds which exhibit high antibacterial activity, inhibiting the growth of a wide variety of pathogenic microorganisms including Gram-positive and Gram-negative bacteria and are useful as antibacterial agents. Particularly, the object compound (I) and pharmaceutically acceptable salt thereof of the present invention are characterized by showing superior blood levels and much longer duration of blood levels. Further, it is to be noted that a syn-isomer of the object compound (I) has much higher antibacterial activities than the corresponding anti-isomer, and accordingly the syn-isomer of the object compound (I) is characterized by having much superiority to the corresponding anti-isomer in the therapeutic value.

Now, in order to show the utility of the object compound (I), with regard to some representative compounds of this invention, the test data on the in vitro anti-bacterial activity are shown in the following.

Test Compounds (1) 7-[2-n-Propoxyimino-2-(2-amino-1,3-thiazol-4-yl)acetamido]-3-(1-carboxymethyl-1H-tetrazol-5-yl)thiomethyl-3-cephem-4-carboxylic acid (syn isomer)

(2) 7-[2-Allyloxyimino-2-(2-amino-1,3-thiazol-4-yl)acetamido]-3-(1-carboxymethyl-1H-tetrazol-5-yl)thiomethyl-3-cephem-4-carboxylic acid hydrochloride (syn isomer)

(3) 7-[2-(2-Propynyloxyimino)-2-(2-amino-1,3-thiazol-4-yl)acetamido]-3-(1-carboxymethyl-1H-tetrazol-5-yl)thiomethyl-3-cephem-4-carboxylic acid (syn isomer)

(4) 7-[2-Methoxyimino-2-(1,2,3-thiadiazol-4-yl)acetamido]-3-(1-carboxymethyl-1H-tetrazol-5-yl)thiomethyl-3-cephem-4-carboxylic acid (syn isomer)

Test Method

In vitro antibacterial activity was determined by the two-fold agar-plate dilution method as described below.

One loopful of an overnight culture of each test strain on Trypticase-soy broth ($10^8$ viable cells per ml.) was streaked on heart infusion agar (HI-agar) containing graded concentrations of test compounds, and minimal inhibitory concentration (MIC) was expressed in terms of µg/ml. after incubation at 37° C. for 20 hours.

Test Results

| (1) Test bacteria | MIC (µg/ml) Test Compound | | |
|---|---|---|---|
| | (1) | (2) | (3) |
| Staphylococcus aureus 209P JC-1 | 12.5 | 12.5 | 12.5 |
| Proteus vulgaris 2 | 0.39 | 0.78 | 0.025 |

| (2) Test Bacteria | MIC (µg/ml) Test Compound (4) |
|---|---|
| Escherichia coli 324 | 0.2 |
| Klebsiella aerogenes 417 | 0.39 |

| Test Results | |
|---|---|
| Proteus mirabilis 525 | 0.2 |

For therapeutic administration, the object compound (I) of the present invention is used in the form of conventional pharmaceutical preparation which contains said compounds, as an active ingredient, in admixture with a pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc., an average single dose of about 50 mg., 100 mg., 250 mg., and 500 mg. of the object compound (I) of the present invention has proved to be effective in treating diseases infected by pathogenic bacteria.

In general, daily dose between 5 mg. and about 3,000 mg. or even more may be administered to a patient.

The folowing examples are given for the purpose of illustrating the present invention:

EXAMPLE 1

(a) Preparation of the starting compound:

(1) Pulverized potassium carbonate (160 g.) was added to a solution of ethyl 2-hydroxyiminoacetoacetate (a mixture of syn and anti isomers) (152 g.) in acetone (500 ml.). Dimethyl sulfate (130 g.) was dropwise added thereto with stirring over 1 hour at 45° to 50° C. and the mixture was stirred for 2 hours. An insoluble material was filtered off and the filtrate was concentrated under reduced pressure. The filtered insoluble material was dissolved in water (500 ml.) and this solution was added to the residue. The mixture was extracted twice with ethyl acetate (300 ml.). The extract was washed twice with water (200 ml.) and with a saturated sodium chloride aqueous solution (200 ml.) and dried over magnesium sulfate. The solvent was distilled off under reduced pressure and the residue was distilled under reduced pressure to give colorless oil of ethyl 2-methoxyiminoacetoacetate (a mixture of syn and anti isomers) (145.3 g.), bp 55° to 64° C./0.5 mm Hg.

I.R. (Film): 1745, 1695, 1600 cm$^{-1}$.

| N.M.R. (CDCl$_3$, δ) | |
|---|---|
| ppm | 4.33 (4H, q, J = 8Hz) |
| | 4.08 (3H, s) |
| | 3.95 (3H, s) |
| | 2.40 (3H, s) |
| | 1.63 (3H, s) |
| | 1.33 (6H, t, J = 8Hz) |

(2) Sulfuryl chloride (235 ml.) was dropwise added over 20 minutes with stirring and ice-cooling to a solution of ethyl 2-methoxyiminoacetoacetate (syn isomer) (500 g.) in acetic acid (500 ml.), and the mixture was stirred overnight under cooling with water. Nitrogen gas was introduced to the reaction mixture for 2 hours, and the resulting mixture was poured into water (2.5 l.) After extracting with methylene chloride (500 ml.) and twice with methylene chloride (200 ml.), the extracts were combined. The combined extracts were washed with a saturated aqueous solution of sodium chloride, and adjusted to pH 6.5 by adding water (800 ml.) and sodium bicarbonate. Methylene chloride layer was separated, washed with an aqueous solution of sodium chloride and dried over magnesium sulfate. The solvent was distilled off to give ethyl 2-methoxyimino-4-chloroacetoacetate (syn isomer) (559 g.).

I.R. (Film): 1735, 1705 cm$^{-1}$.

(3) Ethyl 2-methoxyimino-4-chloroacetoacetate (syn isomer) (50 g.) was added over 3 minutes with stirring at ambient temperature to a solution of thiourea (18.4 g.) and sodium acetate (19.8 g.) in a mixture of methanol (250 ml.) and water (250 ml.). After stirring for 35 minutes at 40° to 45° C., the reaction mixture was cooled with ice and adjusted to pH 6.3 with a saturated aqueous solution of sodium bicarbonate. After stirring for 30 minutes at the same temperature, precipitates were collected by filtration, washed with water (200 ml.) and then with diisopropyl ether (100 ml.), and dried to give colorless crystals of ethyl 2-methoxyimino-2-(2-amino-1,3-thiazol-4-yl)acetate (syn isomer) (37.8 g.), mp 161° to 162° C.

I.R. (Nujol): 3400, 3300, 3150, 1725, 1630, 1559 cm$^{-1}$.

| N.M.R. (CDCl$_3$, δ) | |
|---|---|
| ppm | 6.72 (1H, s) |
| | 5.91 (2H, broad s) |
| | 4.38 (2H, q, J = 7Hz) |
| | 4.03 (3H, s) |
| | 1.38 (3H, t, J = 7Hz) |

(4) A mixture of acetic anhydride (6.1 g.) and formic acid (2.8 g.) was stirred for 2 hours at 50° C. The resulting mixture was cooled and ethyl 2-methoxyimino-2-(2-amino-1,3-thiazol-4-yl)acetate (syn isomer) (4.6 g.) was added thereto at 15° C. After the mixture was stirred for 3.5 hours at ambient temperature, cooled water (100 ml.) was added thereto. The resulting mixture was extracted with ethyl acetate (200 ml.). The extract was washed with water and then with a saturated aqueous solution of sodium bicarbonate until the washing was changed to weakly alkaline solution. The extract was further washed with a saturated aqueous solution of sodium chloride and dried over magnesium sulfate. The solvent was distilled off and the residue was washed with diisopropyl ether, collected by filtration and dried to give ethyl 2-methoxyimino-2-(2-formamido-1,3-thiazol-4-yl)-acetate (syn isomer) (4.22 g.), mp 122° to 124° C. (dec.).

I.R. (Nujol): 3150, 1728, 1700 cm$^{-1}$.

| N.M.R. (CDCl$_3$, δ) | |
|---|---|
| ppm | 12.58 (1H, broad s) |
| | 8.95 (1H, s) |
| | 7.17 (1H, s) |
| | 4.42 (2H, q, J = 8Hz) |
| | 4.00 (3H, s) |
| | 1.37 (3H, t, J = 8Hz) |

(5) A solution of sodium hydroxide (1.6 g.) in water (30 ml.) was dropwise added over 5 minutes with stirring and ice-cooling to a suspension of ethyl 2-methoxyimino-2-(2-formamido-1,3-thiazol-4-yl)acetate (syn isomer) (5.14 g.) in water (60 ml.), and the resulting mixture was stirred for 1.5 hours at 10° to 20° C. The reaction mixture was adjusted to pH 7 with 10% hydrochloric acid and washed twice with ethyl acetate (100 ml.). To the aqueous layer was added ethyl acetate (200 ml.), and the resulting mixture was adjusted to pH 1 with 10% hydrochloric acid and extracted with the ethyl acetate. The aqueous layer was further extracted with ethyl acetate (100 ml.). Both ethyl acetate extracts were combined, washed with a sodium chloride aqueous solution (100 ml.) and dried over magnesium sulfate. The solvent was distilled off to give 2-methoxyimino-2-(2-formamido-1,3-thiazol-4-yl)acetic acid (syn isomer) (1.85 g.), mp 152° C. (dec.), which was recrystallized from ethyl acetate to give a pure compound, mp 167° C. (dec.).

I.R. (Nujol): 3200, 2800-2100, 1950, 1600 cm$^{-1}$.

| N.M.R. ($d_6$ - DMSO, $\delta$) | |
|---|---|
| ppm | 8.60 (1H, s) |
| | 7.62 (1H, s) |
| | 3.98 (1H, s) |

(b) Preparation of the object compound:

Phosphorus oxychloride (1.01 g.) was added under ice-cooling to dry dimethylformamide (0.48 g.) and the mixture was stirred for 30 minutes at 40° C. Dry ethyl acetate (20 ml.) was added thereto and to the suspension was added at 0° to 5° C. 2-methoxyimino-2-(2-formamido-1,3-thiazol-4-yl)acetic acid (syn isomer) (1.26 g.), after which the resulting mixture was vigorously stirred for 30 minutes at the same temperature to give clear yellow solution. On the other hand, trimethylsilylacetamide (6.6 g.) was added to a suspension of 7-amino-3-(1-carboxymethyl-1H-tetrazol-5-yl)thiomethyl-3-cephem-4-carboxylic acid (1.74 g.) in dry ethyl acetate (60 ml.) and the mixture was stirred at ambient temperature to give a clear solution. To this solution was at a time added the above-obtained ethyl acetate solution with stirring at −20° C., and the resulting mixture was stirred for 2 hours at the same temperature. Water (70 ml.) and ethyl acetate (140 ml.) were added thereto and the mixture was shaken. The organic layer was separated and extracted with a sodium bicarbonate aqueous solution (80 ml.). To the aqueous extract was added ethyl acetate (100 ml.) and the mixture was adjusted to pH 1.5 with conc. hydrochloric acid and thereafter shaken. The ethyl acetate layer was separated, washed with a sodium chloride aqueous solution and dried over magnesium sulfate. The solvent was distilled off and the residue was washed with ether, collected by filtration and dried to give 7-[2-methoxyimino-2-(2-formamido-1,3-thiazol-4-yl)acetamido]-3-(1-carboxymethyl-1H-tetrazol-5-yl)thiomethyl-3-cephem-4-carboxylic acid (syn isomer) (2.12 g.).

I.R. (Nujol): 1775, 1670, 1545 cm$^{-1}$.

| N.M.R. ($d_6$ - DMSO, $\delta$) | |
|---|---|
| ppm | 12.63 (1H, broad s) |
| | 9.70 (1H, d, J = 8Hz) |
| | 8.52 (1H, s) |
| | 7.45 (1H, s) |
| | 5.83 (1H, dd, J = 5, 8Hz) |
| | 5.33 (2H, s) |
| | 5.13 (1H, d, J = 5Hz) |
| | 4.36 (2H, AB$_q$, J = 13Hz) |
| | 3.90 (3H, s) |

| -continued |
|---|
| N.M.R. ($d_6$ - DMSO, $\delta$) |
| 3.70 (2H, broad s) |

EXAMPLE 2

(a) Preparation of the starting compound:

(1) A solution of ethyl 2-methoxyiminoacetoacetate (a mixture of syn and anti isomers) (34.6 g.) and tert-butoxycarbonylhydrazine (26.4 g.) in ethanol (200 ml.) was stirred for 7.5 hours at ambient temperature and allowed to stand overnight to precipitate crystals. The crystals were collected by filtration, washed with ethanol and dried to give ethyl 2-methoxyimino-3-tert-butoxycarbonylhydrazonobutyrate (a mixture of syn and anti isomers) (41.7 g.), mp 144° and 145° C.

I.R. (Nujol): 3200, 1750, 1705, 1600, 1520 cm$^{-1}$.

| N.M.R. (CDCl$_3$, $\delta$) | |
|---|---|
| ppm | 8.52 (1H, broad s) |
| | 4.35 (2H, q, J = 7Hz) |
| | 4.10 (3H, s) |
| | 2.00 (3H, s) |
| | 1.50 (9H, s) |
| | 1.33 (3H, t, J = 7Hz) |

(2) Sulfur dichloride (15.9 ml.) was added with stirring at ambient temperature to a solution of ethyl 2-methoxyimino-3-tert-butoxycarbonylhydrazonobutyrate (a mixture of syn and anti isomers) (14.36 g.) in methylene chloride (150 ml.), and the mixture was stirred for 1 hour at ambient temperature. To the reaction mixture was added ice-water (300 ml.), and the methylene chloride layer was washed with water, with a saturated aqueous solution of sodium bicarbonate and with a saturated aqueous solution of sodium chloride and dried over magnesium sulfate. The solvent was distilled off to give an oil. The oil was purified by column chromatography on silica gel using a mixture of benzene and n-hexane (19:1) as an eluent to firstly give ethyl 2-methoxyimino-2-(1,2,3-thiadiazol-4-yl)acetate (syn isomer) (1.8 g.), mp 77° to 79° C.

I.R. (Nujol): 1720, 1595 cm$^{-1}$.

| N.M.R. (CDCl$_3$, $\delta$) | |
|---|---|
| ppm | 8.92 (1H, s) |
| | 4.46 (2H, q, J = 7Hz) |
| | 4.06 (3H, s) |
| | 1.38 (3H, t, J = 7Hz) |

From subsequent fractions, ethyl 2-methoxyimino-2-(1,2,3-thiadiazol-4-yl)acetate (anti isomer) (0.7 g.) was obtained as an oil.

I.R. (Film): 1730, 1590 cm$^{-1}$.

| N.M.R. (CDCl$_3$, $\delta$) | |
|---|---|
| ppm | 9.38 (1H, s) |
| | 4.47 (2H, q, J = 7Hz) |
| | 4.20 (3H, s) |
| | 1.40 (3H, t, J = 7Hz) |

(3) 1 N Aqueous solution of sodium hydroxide (6.7 ml.) was added to a solution of ethyl 2-methoxyimino-2-(1,2,3-thiadiazol-4-yl)acetate (syn isomer) (1.2 g.) in methanol (10 ml.) and the mixture was stirred for 1.5 hours at ambient temperature. Methanol was distilled off from the reaction mixture and water was added to the residue. The mixture was washed with ether, adjusted to pH 1 with 10% hydrochloric acid and extracted with ethyl acetate. The extract was washed with a saturated aqueous solution of sodium chloride and dried over magnesium sulfate. The solvent was distilled off to give prisms of 2-methoxyimino-2-(1,2,3-thiadiazol-4-yl)acetic acid (syn isomer) (0.7 g.), mp 110° to 113° C.

I.R. (Nujol): 2750-2150, 1730, 1595 cm$^{-1}$.

| N.M.R. (d$_6$ - DMSO, δ) | |
|---|---|
| ppm | 9.47 (1H, s) |
| | 4.01 (3H, s) |

(b) Preparation of the object compound:

Phosphorus oxychloride (0.65 g.) was added under ice-cooling to dry dimethylformamide (0.31 g.) and the mixture was stirred for 30 minutes at 40° C. Dry ethyl acetate (15 ml.) was added thereto and to the suspension was added under ice-cooling 2-methoxyimino-2-(1,2,3-thiadiazol-4-yl)-acetic acid (syn isomer) (0.65 g.), after which the resulting mixture was vigorously stirred for 30 minutes at the same temperature to give a solution. On the other hand, trimethylsilylacetamide (4.20 g.) was added to a suspension of 7-amino-3-(1-carboxymethyl-1H-tetrazol-5-yl)thiomethyl-3-cephem-4-carboxylic acid (1.20 g.) in dry ethyl acetate (50 ml.), and the mixture was stirred for 2.5 hours at ambient temperature. To this suspension was at a time added at −20° C. the above-obtained ethyl acetate solution, and the resulting mixture was stirred for 1.5 hours at the same temperature. The reaction mixture was extracted after addition of ethyl acetate (70 ml.) and water (35 ml.). The organic layer was extracted with a sodium bicarbonate aqueous solution (35 ml.). To the aqueous extract was added ethyl acetate (70 ml.), and the mixture was adjusted to pH 2.0 with conc. hydrochloric acid with stirring and then the ethyl acetate layer was separated. The ethyl acetate layer was washed with a sodium chloride aqueous solution and dried over magnesium sulfate. The solvent was distilled off to give white powder of 7-[2-methoxyimino-2-(1,2,3-thiadiazol-4-yl)acetamido]-3-(1-carboxymethyl-1H-tetrazol-5-yl)thiomethyl-3-cephem-4-carboxylic acid (syn isomer) (1.36 g.).

I.R. (Nujol): 1775, 1720, 1665, 1540 cm$^{-1}$.

| N.M.R. (d$_6$ - DMSO, δ) | |
|---|---|
| ppm | 9.85 (1H, d, J = 8Hz) |
| | 9.40 (1H, s) |
| | 5.88 (1H, dd, J = 4,8Hz) |
| | 5.40 (2H, s) |
| | 5.17 (1H, d, J = 4Hz) |
| | 4.36 (2H, AB$_q$, J = 12Hz) |
| | 4.00 (3H, s) |
| | 3.70 (2H, AB$_q$, J = 16Hz) |

EXAMPLE 3

(a) Preparation of the starting compound:

(1) To a solution of ethyl 2-(2-amino-1,3-thiazol-4-yl)acetate (14 g.) in a mixture of pyridine (40 g.) and methylene chloride (300 ml.) was gradually added diethyl ether solution of tert-pentyl chloroformate (70 ml.) containing 0.35 mole of tert-pentyl chloroformate over 10 minutes at −20° C. with stirring, and the mixture was stirred for 2 hours at the same temperature and further stirred for 0.5 hour at 0° C. After the reaction, the reaction mixture was poured into water (200 ml.), and then the organic layer was separated. The organic layer was washed with 2 N hydrochloric acid, water, 5% sodium bicarbonate aqueous solution and water in turn and then dried over magnesium sulfate. The solvent was distilled off from the organic layer to give dark brown oil of ethyl 2-(2-tert-pentyloxycarbonylamino-1,3-thiazol-4-yl)acetate (12 g.).

I.R. (liquid): 1667, 1660 (CO) cm$^{-1}$.

| N.M.R. (CDCl$_3$, δ) | |
|---|---|
| ppm | 3.75 (2H, s) |
| | 6.75 (1H, s) |

(2) To a solution of selenium dioxide (0.11 g.) in a mixture of dioxane (2.5 ml.) and water (0.1 ml.) was added a mixture of ethyl 2-(2-tert-pentyloxycarbonylamino-1,3-thiazol-4-yl)acetate (0.3 g.) and dioxane (2.5 ml.) at 110° C. with stirring. The mixture was stirred for 30 minutes at the same temperature, and selenium dioxide (0.055 g.) was further added thereto and then the mixture was stirred for 1.5 hours at the same temperature. After the reaction, the reaction liquid is separated by decantation, and the residue was washed with a small amount of dioxane. The reaction liquid and washing were combined together, and then the solvents were distilled off. The residue was dissolved in ethyl acetate. The solution was washed with water and dried and then the solvent was distilled off to give brown oil of ethyl 2-(2-tert-pentyloxycarbonylamino-1,3-thiazol-4-yl)glyoxylate (0.22 g.).

I.R. (liquid): 1720, 1690 (CO) cm$^{-1}$.

| N.M.R. (CDCl$_3$, δ) | |
|---|---|
| ppm | 8.3 (1H, s) |

(3) A mixture of ethyl 2-(2-tert-pentyloxycarbonylamino-1,3-thiazol-4-yl)glyoxylate (2.8 g.) and ethanol (10 ml.) was mixed with a solution of sodium hydroxide (0.54 g.) in water (20 ml.), and the mixture was stirred for 1 hour at room temperature. After the reaction, a small amount of ethanol was distilled off. The remaining reaction mixture was washed with diethyl ether and then the aqueous layer was separated therefrom. To the aqueous layer was added ethyl acetate, and the mixture was adjusted to pH 1 to 2 with 10% hydrochloric acid and then the ethyl acetate layer was separated therefrom. The ethyl acetate layer was washed with a saturated aqueous solution of sodium chloride, dried over magnesium sulfate and then treated with activated charcoal. The solvent was distilled off from the ethyl acetate layer to give yellow brown powder of 2-(2-1-tert-pentyloxycarbonylamino-1,3-thiazol-4-yl)glyoxylic acid (1.75 g.).

I.R. (Nujol): 1730, 1680 (CO) cm$^{-1}$.

| N.M.R. (d$_6$ - dimethylsulfoxide, δ) | |
|---|---|
| ppm | 8.4 (1H, s) |

(b) Preparation of the object compound:

Phosphorus oxychloride (0.66 g.) was added under ice-cooling to dry dimethylformamide (b 0.52 g.) and the mixture was stirred for 30 minutes at 40° C. Dry ethyl acetate (15 ml.) was added thereto and to the suspension was at a time added at −13° C. 2-(2-tert-pentyloxycarbonylamino-1,3-thiazol-4-yl)glyoxylic acid (1.03 g.) to give a clear solution, which was stirred for 30 minutes at the same temperature. On the other hand, trimethylsilylacetamide (5.10 g.) was added to a suspension of 7-amino-3-(1-carboxymethyl-1H-tetrazol-5-yl)thiomethyl-3-cephem-4-carboxylic acid (1.45 g.) in dry ethyl acetate (55 ml.). To this suspension was at a time added at −20° C. the above-obtained ethyl acetate solution, and the mixture was stirred for 1.5 hours at the same temperature. To the reaction mixture was added water (15 ml.) and the mixture was shaken. The organic layer was extracted with 10% sodium bicarbonate aqueous solution (30 ml.). To the extract was added ethyl acetate (75 ml.), and the mixture was adjusted to pH 2.0 with conc. hydrochloric acid with stirring and the ethyl acetate layer was separated. The ethyl acetate layer was dried over magnesium sulfate and treated with an activated charcoal. The solvent was distilled off to give white powder of 7-[2-(2-tert-pentyloxycarbonylamino-1,3-thiazol-4-yl)glyoxylamido]-3-(1-carboxymethyl-1H-tetrazol-5-yl)thiomethyl-3-cephem-4-carboxylic acid (0.92 g.).

I.R. (Nujol): 1780, 1725, 1680, 1560 cm$^{-1}$.

| N.M.R. (d$_6$ - DMSO, δ) | |
|---|---|
| ppm | 9.90 (1H, d, J = 8Hz) |
| | 8.45 (1H, s) |
| | 5.80 (1H, dd, J = 5,8Hz) |
| | 5.30 (2H, s) |
| | 5.15 (1H, d, J = 5Hz) |
| | 4.40 (2H, AB$_q$, J = 13Hz) |
| | 3.70 (2H, broad s) |
| | 1.8 (2H, q, J = 8Hz) |
| | 1.45 (6H, s) |
| | 0.90 (3H, t, J = 8Hz) |

EXAMPLE 4

The following compound was obtained according to similar manners to those of Examples 1 to 3. 7-[2-(2-amino-1,3-thiazol-4-yl)glyoxylamido]-3-(1-carboxymethyl-1H-tetrazol-5-yl)thiomethyl-3-cephem-4-carboxylic acid.

I.R. (Nujol): 1780, 1665, 1520 cm$^{-1}$.

| N.M.R. (d$_6$ - DMSO, δ) | |
|---|---|
| ppm | 9.80 (1H, d, J = 8Hz) |
| | 7.93 (1H, s) |
| | 5.80 (1H, dd, J = 5,8Hz) |
| | 5.37 (2H, s) |
| | 5.20 (1H, d, J = 5Hz) |
| | 4.40 (2H, AB$_q$, J = 13Hz) |
| | 3.73 (2H, broad s) |

EXAMPLE 5

A mixture of 7-[2-(2-tert-pentyloxycarbonylamino-1,3-thiazol-4-yl)glyoxylamido]-3-(1-carboxymethyl-1H-tetrazol-5-yl)thiomethyl-3-cephem-4-carboxylic acid (870 mg.) and 99% formic acid (16 ml.) was stirred for 3.5 hours at ambient temperature. The solvent was distilled off and to the residue was added diethyl ether (20 ml.). Insoluble material was collected by filtration and dissolved in 5% sodium bicarbonate aqueous solution (20 ml.) The aqueous solution was washed with ethyl acetate (20 ml.) and to the resulting aqueous solution was added ethyl acetate (60 ml.). The mixture was adjusted to pH 2.0 with 10% hydrochloric acid with stirring to precipitate powder. The precipitates were collected by filtration, well stirred in ethyl acetate (50 ml.) to remove impurities and collected by filtration to give 7-[2-(2-amino-1,3-thiazol-4-yl)glyoxylamido]-3-(1-carboxymethyl-1H-tetrazol-5-yl)thiomethyl-3-cephem-4-carboxylic acid (240 mg.). The aqueous layer in the filtrate of pH 2.0 as mentioned above was separated and allowed to stand overnight. Precipitates were collected by filtration further to give the same object compound (120 mg.). Total yield 360 mg.

I.R. (Nujol): 1780, 1665, 1520 cm$^{-1}$.

| N.M.R. (d$_6$ - DMSO, δ) | |
|---|---|
| ppm | 9.80 (1H, d, J = 8Hz) |
| | 7.93 (1H, s) |
| | 5.80 (1H, dd, J = 5,8Hz) |
| | 5.37 (2H, s) |
| | 5.20 (1H, d, J = 5Hz) |
| | 4.40 (2H, AB$_q$, J = 13Hz) |
| | 3.73 (2H, broad s) |

EXAMPLE 6

(a) Preparation of the starting compound:

(1) A solution of ethyl 2-methoxyimino-3-oxo-4-chlorobutyrate (41.4 g.) in dried chloroform (100 ml.) was added dropwise over 1 hour at 20° C. to a mixture of ethane-1,2-dithiol (20.6 g.), triethylamine (21 g.) and dried chloroform (60 ml.). After stirring for 2.5 hours at 18 to 21° C., the mixture was adjusted to pH 1.0 with 10% hydrochloric acid. The chloroform layer was separated, washed with water (100 ml.×3), dried over magnesium sulfate and concentrated to dryness under reduced pressure at 40° C. The residue was dissolved in toluene (300 ml.), p-toluenesulfonic acid (3 g.) was added thereto and the resulting mixture was refluxed for 3 hours with removal of water. The reaction mixture was cooled to ambient temperature and an insoluble material was filtered off. The filtrate was concentrated under reduced pressure at 40° C. The residue was dissolved in ethyl acetate (300 ml.). The solution was in turn washed with a saturated aqueous solution of sodium bicarbonate (3 times) and water (twice), dried over magnesium sulfate and concentrated to dryness under reduced pressure at 40° C. to give yellow oil. The oil was subjected to column chromatography on silica gel (1 kg) and eluted with benzene. The eluate was concentrated under reduced pressure at 40° C. The residue was washed with diisopropyl ether and dried to give white crystals of ethyl 2-methoxyimino-2-(2,3-dihydro-1,4-dithiin-5-yl)acetate (syn isomer) (11 g.), mp. 65° to 67° C.

I.R. (Nujol): 1725, 1670 cm$^{-1}$.

N.M.R. (d$_6$-DMSO, δ): 6.78 (1H, s), 4.30 (2H, q, J=7 Hz), 3.80 (3H, s), 3.25 (4H, s), 1.25 (3H, t, J=7 Hz).

(2) Ethyl 2-methoxyimino-2-(2,3-dihydro-1,4-dithiin-5-yl)acetate (syn isomer) (2.47 g) was treated with 1 N aqueous solution of sodium hydroxide (20 ml.) according to similar manners to those of Examples 1 (a) (5), 2 (a) (3) and 3(a) (3) to give 2-methoxyimino-2-(2,3-dihydro-1,4-dithiin-5-yl)acetic acid (syn isomer) (2.0 g.), mp. 120° to 122° C. (dec.).

I.R. (Nujol): 2500~2600, 1720, 1670, 1620 cm$^{-1}$.

N.M.R. (d$_6$-DMSO, δ): 6.61 (1H, s), 3.80 (3H, s), 3.20 (4H, s).

(b) Preparation of the object compound:

The Vilsmeier reagent was prepared from dry dimethylformamide (0.80 g.), phosphorus oxychloride (1.67 g.) and ethyl acetate (4 ml.) according to a similar manner to that of Example 1.

Ethyl acetate (15 ml.) and 2-methoxyimino-2-(2,3-dihydro-1,4-dithiin-5-yl)acetic acid (syn isomer) (2.0 g.) were added to the solution at −10° C. to give a solution. On the other hand, a suspension of 7-amino-3-(1-carboxymethyl-1H-tetrazol-5-yl)thiomethyl-3-cephem-4-carboxylic acid (2.83 g.) in water (40 ml.) was changed to a solution by adding sodium bicarbonate (1.45 g.), and then acetone (40 ml.) was added thereto. After the solution was adjusted to pH 7.3, the ethyl acetate solution obtained above was added dropwise thereto over 10 minutes with stirring at −5° to −7° C., during which the pH of the mixture was kept at 6.8 to 7.3 with an aqueous solution of sodium bicarbonate. The mixture was stirred for 1.5 hours at the same temperature. The resultant solution was adjusted to pH 7.8 and washed with ethyl acetate (40 ml.). The solution was adjusted to pH 6 and washed with ethyl acetate (40 ml.). And the solution was adjusted to pH 2 and extracted with ethyl acetate (100 ml.). The extract was washed with a saturated aqueous solution of sodium chloride (60 ml.) and dried over magnesium sulfate. The extract was concentrated in vacuo, and the residue was washed with diethyl ether and collected by filtration to give pale yellow crystals of 7-[2-methoxyimino-2-(2,3-dihydro-1,4-dithiin-5-yl)acetamido]-3-(1-carboxymethyl-1H-tetrazol-5-yl)thiomethyl-3-cephem-4-carboxylic acid (syn isomer) (3.4 g.).

I.R. (Nujol): 3200, 1765, 1730, 1660 cm$^{-1}$.

N.M.R. (d$_6$-DMSO, δ): 9.79 (1H, d, J=8 Hz), 6.65 (1H, s), 5.78 (1H, dd, J=5, 8 Hz), 5.35 (2H, s), 5.15 (1H, d, J=5 Hz), 4.40 (2H, AB$_q$, J=13 Hz), 3.85 (3H, s), 3.73 (2H, broad s), 3.23 (4H, s).

EXAMPLE 7

(a) Preparation of the starting compound:

(1) To a suspension of ethyl 2-hydroxyimino-3-oxobutyrate (syn isomer) (15 g.) and potassium carbonate (19.8 g.) in acetone (75 ml.) was added dropwise n-propyl iodide (16.2 g.) with stirring, and the mixture was stirred at ambient temperature for 1.5 hours. The insoluble substance was collected by filtration and washed with acetone. The washings and the filtrate were combined and evaporated to dryness under reduced pressure. To the resultant residue was added water and the aqueous solution was extracted twice with chloroform. The extract was washed with an aqueous solution of sodium chloride, dried over magnesium sulfate, and then evaporated to dryness under reduced pressure to give ethyl 3-oxo-2-n-propoxyiminobutyrate (syn isomer) (15.4 g.), oil.

(2) Ethyl 3-oxo-2-n-propoxyiminobutyrate (syn isomer) (15.4 g.) and sulfuryl chloride (10.6 g.) were dissolved in acetic acid (15.4 ml.), warmed at 35° to 40° C. for 10 minutes with stirring and then stirred at ambient temperature for additional 6 hours. The reaction mixture was poured into ice-water (200 ml.) and the resultant mixture was extracted twice with chloroform. The extract was washed with an aqueous solution of sodium chloride, twice a saturated aqueous solution of sodium bicarbonate and once with water in turn, dried over magnesium sulfate, and then evaporated to dryness under reduced pressure to give ethyl 4-chloro-3-oxo-2-n-propoxyiminobutyrate (syn isomer) (15.4 g.), oil.

I.R. (Film): 1740, 1710, 1695, 1455 cm$^{-1}$.

(3) Ethyl 4-chloro-3-oxo-2-n-propoxyiminobutyrate (syn isomer) (15.4 g.), thiourea (4.97 g.) and sodium acetate hydrate (8.89 g.) were dissolved in a mixture of water (40 ml.) and ethanol (50 ml.), and stirred at 40° C. for an hour. The reaction mixture was adjusted to pH 6.5 with a saturated aqueous solution of potassium carbonate under cooling and stirred at the same temperature for half an hour. The precipitating crystals were collected by filtration, washed with water and diisopropyl ether, and then dried to give crystalline ethyl 2-n-propoxyimino-2-(2-amino-1,3-thiazol-4-yl)acetate (syn isomer) (10.55 g.), mp 142° to 144° C.

I.R. (Nujol): 3460, 3260, 3120, 1720, 1620, 1540 cm$^{-1}$.

N.M.R. (d$_6$-DMSO, δ) 0.88 (3H, t, J=7 Hz), 1.27 (3H, t, J=6 Hz), 1.60 (2H, sextet, J=7 Hz), 4.04 (2H, t, J=7 Hz), 4.28 (2H, q, J=6 Hz), 6.86 (1H, s), 7.23 (2H, s).

(4) A solution of ethyl 2-n-propoxyimino-2-(2-amino-1,3-thiazol-4-yl)acetate (syn isomer) (10 g.) in a mixture of tetrahydrofuran (39 ml.), methanol (39 ml.) and 1 N sodium hydroxide (75.8 ml.) was stirred at 35° to 40° C. for 5 hours. After the resultant solution was concentrated under reduced pressure, the aqueous residue was adjusted to pH 2.5 with 10% hydrochloric acid. The precipitates were collected by filtration and dried to give 2-n-propoxyimino-2-(2-amino-1,3-thiazol-4-yl)acetic acid (syn isomer) (6.2 g.), mp. 161° C. (dec.).

I.R. (Nujol): 3380, 3120 (broad), 1630, 1610, 1460 cm$^{-1}$.

N.M.R. (d$_6$-DMSO, δ): 0.89 (3H, t, J=7 Hz), 1.63 (2H, sextet, J=7 Hz), 4.05 (2H, t, J=7 Hz), 6.83 (1H, s), 6.9~8.8 (3H, broad).

(5) Formic acid (17.5 g.) was added dropwise to acetic anhydride (38.8 g.) over 3 to 4 minutes with stirring and ice-cooling, and the mixture was stirred for 1 hour at 50° C. 2-n-Propoxyimino-2-(2-amino-1,3-thiazol-4-yl)acetic acid (syn isomer) (21.8 g.) was added thereto with stirring and ice-cooling, and the mixture was stirred for 2.5 hours at ambient temperature. The reaction mixture was concentrated to dryness under reduced pressure, and the residue was pulverized with diisopropyl ether. The powder was collected by filtration and dried to give 2-n-propoxyimino-2-(2-formamido-1,3-thiazol-4-yl)acetic acid (syn isomer) (19.2 g.).

I.R. (Nujol): 3200, 3120, 3050, 1700, 1550 cm$^{-1}$.

N.M.R. (d$_6$-DMSO, δ): 8.54 (1H, s), 7.53 (1H, s), 4.12 (2H, t, J=7 Hz), 1.67 (2H, sextet, J=7 Hz), 0.92 (3H, t, J=7 Hz).

(b) Preparation of the object compound:

2-n-Propoxyimino-2-(2-formamido-1,3-thiazol-4-yl)acetic acid (syn isomer) (1.73 g.) and 7-amino-3-(1-carboxymethyl-1H-tetrazol-5-yl)thiomethyl-3-cephem-4-carboxylic acid (2.0 g.) were reacted according to similar manners to those of Examples 1(b), 2(b), 3(b) and 6(b) to give white powder of 7-[2-n-propoxyimino-2-(2-formamido-1,3-thiazol-4-yl)acetamido]-3-(1-carboxymethyl-1H-tetrazol-5-yl)thiomethyl-3-cephem-4-carboxylic acid (syn isomer) (2.32 g.).

I.R. (Nujol): 3180, 1770, 1710, 1650 cm$^{-1}$.

N.M.R. (d$_6$-DMSO, δ): 9.57 (1H, d, J=8 Hz), 8.50 (1H, s), 7.35 (1H, s), 5.80 (1H, dd, J=5, 8 Hz), 5.28 (2H, s), 5.10-(1H, d, J=5 Hz), 4.33 (2H, AB$_q$, J=13 Hz), 4.03 (2H, t, J=7 Hz), 3.63 (2H, broad s), 1.67 (2H, m), 0.90 (3H, t, J=7 Hz).

EXAMPLE 8

2-Methoxyimino-2-(3-hydroxyphenyl)acetic acid (syn isomer) (1.33 g.) and 7-amino-3-(1-carboxymethyl-1H-tetrazol-5-yl)thiomethyl-3-cephem-4-carboxylic acid (3 g.) were reacted according to similar manners to those of Examples 1(b), 2(b), 3(b) and 6(b) to give powder of 7-[2-methoxyimino-2-(3-hydroxyphenyl)acetamido]-3-(1-carboxymethyl-1H-tetrazol-5-yl)thiomethyl-3-cephem-4-carboxylic acid (syn isomer) (1.447 g.).

I.R. (Nujol): 1767 cm$^{-1}$.

N.M.R. (d$_6$-DMSO, δ): 9.68 (1H, d, J=8 Hz), 6.76~7.36 (4H, m), 5.68 (1H, dd, J=4.2, 8 Hz), 5.06 (1H, d, J=4.2 Hz), 4.66 (2H, s), 4.34 (2H, m), 3.90 (3H, s).

EXAMPLE 9

The Vilsmeier reagent was prepared by conventional method from dimethylformamide (1.16 g.), phosphorus oxychloride (2.44 g.) and ethyl acetate (6 ml.). Ethyl acetate (10 ml.) was added thereto, and then a solution of 2-dichloroacetoxyimino-2-(3-hydroxyphenyl)acetic acid (syn isomer) (4.03 g.) in ethyl acetate (28 ml.) was added thereto with stirring at −10° C., after which the resulting mixture was stirred for 30 minutes at the same temperature to give a solution. On the other hand, a suspension of 7-amino-3-(1-carboxymethyl-1H-tetrazol-5-yl)thiomethyl-3-cephem-4-carboxylic acid (4.30 g.) in water (25 ml.) was dissolved by adding a saturated aqueous solution of sodium bicarbonate and acetone (50 ml.) was added thereto to adjust the pH of the solution at 7.5. To this solution was added dropwise with stirring at −10° C. the ethyl acetate solution obtained above, and then the resulting mixture was stirred for 1 hour at the same temperature, during which the pH of the mixture was kept at 6.5 to 7.0. The reaction mixture was adjusted to pH 5.5 and washed with ethyl acetate (60 ml.). The aqueous layer was adjusted to pH 2.0 and extracted with ethyl acetate (400 ml.). The extract was washed with a saturated aqueous solution of sodium chloride, dried over magnesium sulfate and concentrated. The residue was pulverized with diethyl ether and the powder was collected by filtration to give 7-[2-hydroxyimino-2-(3-hydroxyphenyl)acetamido]-3-(1-carboxymethyl-1H-tetrazol-5-yl)thiomethyl-3-cephem-4-carboxylic acid (syn isomer) (4.11 g.).

I.R. (Nujol): 3250, 1760, 1660 cm$^{-1}$.

N.M.R. (d$_6$-DMSO, δ): 10.97 (1H, s), 9.60 (1H, d, J=8 Hz), 7.10 (4H, m), 5.87 (1H, dd, J=5, 8 Hz), 5.33 (2H, s), 5.17 (1H, d, J=5 Hz), 4.40 (2H, AB$_q$, J=14 Hz), 3.70 (2H, broad s)

EXAMPLE 10

(a) Preparation of the starting compound:

(1) Sulfuryl chloride (35.2 g.) was added all at once to the stirred solution of ethyl 2-ethoxyimino-3-oxobutyrate (syn isomer) (48.9 g.) in acetic acid (49 ml.) at room temperature, and stirred at the same temperature for an hour. After adding the resultant solution into water (200 ml.), the solution was extracted with methylene chloride. The extract was washed with a saturated aqueous solution of sodium chloride, neutralized with an aqueous solution of sodium bicarbonate and washed with water. The solution was dried over magnesium sulfate and concentrated under reduced pressure to give ethyl 2-ethoxyimino-3-oxo-4-chlorobutyrate (syn isomer) (53.8 g.), pale yellow oil.

(2) A mixture of ethyl 2-ethoxyimino-3-oxo-4-chlorobutyrate (syn isomer) (38.7 g.), thiourea (13.2 g.), sodium acetate (14.3 g.), methanol (95 ml.) and water (95 ml.) was stirred at 48° C. for 40 minutes. After the resultant solution was adjusted to pH 6.5 with an aqueous solution of sodium bicarbonate, the appeared precipitates were collected by filtration and washed with diisopropyl ether to give ethyl 2-ethoxyimino-2-(2-amino-1,3-thiazol-4-yl)acetate (syn isomer) (14.7 g.), mp. 130° to 131° C.

I.R. (Nujol): 3450, 3275, 3125, 1715, 1620 cm$^{-1}$.

(3) Ethyl 2-ethoxyimino-2-(2-amino-1,3-thiazol-4-yl)acetate (syn isomer) (5 g.) was added to a mixture of 1 N sodium hydroxide (45.9 ml.) and ethanol (30 ml.) and stirred at ambient temperature for 5 hours. After removing ethanol from the resultant solution under reduced pressure, the residue was dissolved in water (60 ml.) and adjusted to pH 2.0 with 10% hydrochloric acid. The solution was subjected to salting-out, and the precipitates were collected by filtration and dried to give 2-ethoxyimino-2-(2-amino-1,3-thiazol-4-yl)acetic acid (syn isomer) (2.9 g.).

I.R. (Nujol): 3625, 3225 (shoulder), 3100, 1650, 1615 cm$^{-1}$.

N.M.R. (d$_6$-DMSO, δ): 1.20 (3H, t, J=7 Hz), 4.09 (2H, q, J=7 Hz), 6.82 (1H, s), 7.24 (2H, broad s)

(4) 2-Ethoxyimino-2-(2-amino-1,3-thiazol-4-yl)acetic acid (syn isomer) (100 g.), formic acid (85.5 g.) and acetic anhydride (190.1 g.) were treated according to a similar manner to that of Example 7(a) 5) to give 2-ethoxyimino-2-(2-formamido-1,3-thiazol-4-yl)acetic acid (syn isomer) (99.1 g.).

I.R. (Nujol): 3200, 3140, 3050, 1700 cm$^{-1}$.

N.M.R. (d$_6$-DMSO, δ): 12.62 (1H, broad s), 8.56 (1H, s), 7.56 (1H, s), 4.22 (2H, q, J=6 Hz), 1.18 (3H, t, J=6 Hz).

(b) Preparation of the object compound:

2-Ethoxyimino-2-(2-formamido-1,3-thiazol-4-yl)acetic acid (syn isomer) (3.0 g.) and 7-amino-3-(1-carboxymethyl-1H-tetrazol-5-yl)thiomethyl-3-cephem-4-carboxylic acid (4.12 g.) were reacted according to similar manners to those of Examples 1(b), 2(b), 3(b) and 6(b) to give 7-[2-ethoxyimino-2-(2-formamido-1,3-thiazol-4-yl)acetamido]-3-(1-carboxymethyl-1H-tetrazol-5-yl)thiomethyl-3-cephem-4-carboxylic acid (syn isomer) (3.6 g.).

I.R. (Nujol): 3180, 1770, 1710, 1665, 1640 cm$^{-1}$.

N.M.R. (d$_6$-DMSO, δ): 9.87 (1H, d, J=8 Hz), 8.57 (1H, s), 7.43 (1H, s), 5.87 (1H, dd, J=5, 8 Hz), 5.32 (2H, s), 5.18 (1H, d, J=5 Hz), 4.40 (2H, AB$_q$, J=14 Hz), 4.20 (2H, q, J=7 Hz), 3.70 (2H, broad s), 1.27 (3H, t, J=7 Hz).

EXAMPLE 11

The following compounds were obtained according to similar manners to those of Examples 1 to 3 and 6.

(1) 7-[2-Ethoxyimino-2-(2-amino-1,3-thiazol-4-yl)acetamido]-3-(1-carboxymethyl-1H-tetrazol-5-yl)thiomethyl-3-cephem-4-carboxylic acid (syn isomer).

I.R. (Nujol): 3280, 1770, 1655 cm$^{-1}$.

N.M.R. (d$_6$-DMSO, δ): 9.60 (1H, d, J=8 Hz), 7.20 (2H, broad s), 6.78 (1H, s), 5.83 (1H, dd, J=5, 8 Hz), 5.33 (2H, s), 5.15 (1H, d, J=8 Hz), 4.35 (2H, AB$_q$, J=14 Hz), 4.15 (2H, t, J=7 Hz), 3.70 (2H, broad s), 1.25 (3H, t, J=7 Hz).

(2) 7-[2-n-Propoxyimino-2-(2-amino-1,3-thiazol-4-yl)acetamido]-3-(1-carboxymethyl-1H-tetrazol-5-yl)thiomethyl-3-cephem-4-carboxylic acid (syn isomer).

I.R. (Nujol): 3350, 1775, 1660 cm$^{-1}$.

N.M.R. (d$_6$-DMSO, δ) 9.53 (1H, d, J=8 Hz), 7.17 (2H, broad s), 6.70 (1H, s), 5.80 (1H, dd, J=5, 8 Hz), 5.20 (2H, s), 5.10 (1H, d, J=5 Hz), 4.35 (2H, AB$_q$, J=13 Hz), 4.00 (2H, t, J=7 Hz), 3.67 (2H, broad s), 1.63 (2H, m), 0.90 (3H, t, J=7 Hz).

(3) 7-[2-Methoxyimino-2-(3-aminophenyl)acetamido]-3-(1-carboxymethyl-1H-tetrazol-5-yl)thiomethyl-3-cephem-4-carboxylic acid (syn isomer).

I.R. (Nujol): 3600~3100, 1780, 1670, 1650, 1540, 1240, 890, 815 cm$^{-1}$.

N.M.R. (d$_6$-DMSO+D$_2$O, δ): 7.44 (1H, t, J=7 Hz), 6.89 (1H, s), 6.84 (2H, m), 5.82 (1H, d, J=5 Hz), 5.30 (2H, s), 5.12 (1H, d, J=5 Hz), 4.48 (1H, d, J=13 Hz), 4.20 (1H, d, J=13 Hz), 3.90 (3H, s), 3.6 (2H, m).

(4) 7-[2-Methoxyimino-2-(3-formamidophenyl)acetamido]-3-(1-carboxymethyl-1H-tetrazol-5-yl)thiomethyl-3-cephem-4-carboxylic acid (syn isomer), foamy substance.

EXAMPLE 12

Conc. hydrochloric acid (0.54 g.) was added dropwise at ambient temperature to a suspension of 7-[2-ethoxyimino-2-(2-formamido-1,3-thiazol-4-yl)acetamido]-3-(1-carboxymethyl-1H-tetrazol-5-yl)thiomethyl-3-cephem-4-carboxylic acid (syn isomer) (2.7 g.) in methanol (70 ml.), and the resulting mixture was stirred for 4.5 hours at ambient temperature. The solvent was distilled off under reduced pressure and water (30 ml.) was added to the residue. The mixture was adjusted to pH 7.2 with a saturated aqueous solution of sodium bicarbonate, and an insoluble material was filtered off. The filtrate was washed with ethyl acetate (25 ml.) and then in turn adjusted to pH 5.5, 4.5 and 3.8, and in turn washed with ethyl acetate at each pH. The aqueous layer was adjusted to pH 1.7, and precipitates were collected by filtration, washed with water (200 ml.) and dried under reduced pressure to give 7-[2-ethoxyimino-2-(2-amino-1,3-thiazol-4-yl)acetamido]-3-(1-carboxymethyl-1H-tetrazol-5-yl)thiomethyl-3-cephem-4-carboxylic acid (syn isomer) (1.65 g.).

I.R. (Nujol): 3280, 1770, 1655 cm$^{-1}$.

N.M.R. (d$_6$-DMSO, δ): 9.60 (1H, d, J=8 Hz), 7.20 (2H, broad s), 6.78 (1H, s), 5.83 (1H, dd, J=5, 8 Hz), 5.33 (2H, s), 5.15 (1H, d, J=8 Hz), 4.35 (2H, AB$_q$, J=14 Hz), 4.15 (2H, t, J=7 Hz), 3.70 (2H, broad s), 1.25 (3H, t, J=7 Hz).

EXAMPLE 13

7-[2-n-Propoxyimino-2-(2-formamido-1,3-thiazol-4-yl)acetamido]-3-(1-carboxymethyl-1H-tetrazol-5-yl)thiomethyl-3-cephem-4-carboxylic acid (syn isomer) (2.20 g.) was treated with conc. hydrochloric acid (0.56 g.) according to a similar manner to that of Example 12 to give 7-[2-n-propoxyimino-2-(2-amino-1,3-thiazol-4-yl)acetamido]-3-(1-carboxymethyl-1H-tetrazol-5-yl)thiomethyl-3-cephem-4-carboxylic acid (syn isomer) (1.10 g.).

I.R. (Nujol): 3350, 1775, 1660 cm$^{-1}$.

N.M.R. (d$_6$-DMSO, δ): 9.53 (1H, d, J=8 Hz), 7.17 (2H, broad s), 6.70 (1H, s), 5.80 (1H, dd, J=5, 8 Hz), 5.20 (2H, s), 5.10 (1H, d, J=5 Hz), 4.35 (2H, AB$_q$, J=13 Hz), 4.00 2H, t, J=7 Hz), 3.67 (2H, broad s), 1.63 (2H, m), 0.90 (3H, t, J=7 Hz).

EXAMPLE 14

The following compound was obtained according to similar manners to those of Examples 5 and 12.

7-[2-Methoxyimino-2-(3-aminophenyl)acetamido]-3-(1-carboxymethyl-1H-tetrazol-5-yl)thiomethyl-3-cephem-4-carboxylic acid (syn isomer).

I.R. (Nujol): 3600~3100, 1780, 1670, 1650, 1540, 1240, 890, 815 cm$^{-1}$.

N.M.R. (d$_6$-DMSO+D$_2$O, δ): 7.44 (1H, t, J=7 Hz), 6.89 (1H, s), 6.84 (2H, m), 5.82 (1H, d, J=5 Hz), 5.30 (2H, s), 5.12 (1H, d, J=5 Hz), 4.48 (1H, d, J=13 Hz), 4.20 (1H, d, J=13 Hz), 3.90 (3H, s), 3.6 (2H, m).

EXAMPLE 15

A saturated aqueous solution of sodium bicarbonate was added to a suspension of 7-[2-methoxyimino-2-(3-formamidophenyl)acetamido]cephalosporanic acid (syn isomer) (3.2 g) and disodium (5-sulfido-1H-tetrazol-1-yl)acetate (4.14 g) in pH 6.4 phosphate buffer solution (60 ml) to give a clear solution and to adjust the pH of the solution at 7.0 to 7.3. The solution was stirred for 8 hours at 60° to 62° C. keeping the pH at 7.0 to 7.3 by adding a saturated aqueous solution of sodium bicarbonate. The reaction mixture was adjusted to pH 5.5 with dil. hydrochloric acid, washed with ethyl acetate (twice), adjusted to pH 2.5 and extracted with ethyl acetate (80 mlx 3). The extracts were washed with an aqueous solution of sodium chloride, dried over magnesium sulfate, treated with an activated charcoal and concentrated to give foamy substance of 7-[2-methoxyimino-2-(3-formamidophenyl)acetamido]-3-(1-carboxymethyl-1H -tetrazol-5-yl)thiomethyl-3-cephem-4-carboxylic acid (syn isomer) (4.1 g).

EXAMPLE 16

The following compounds were obtained according to a similar manner to that of Example 15.

(1) 7-[2-Methoxyimino-2-(2-formamido-1,3-thiazol-4-yl)-acetamido]-3-(1-carboxymethyl-1H-tetrazol-5-yl)thiomethyl-3-cephem-4-carboxylic acid (syn isomer).

I.R. (Nujol): 1775, 1670, 1545 cm$^{-1}$.

N.M.R. (d$_6$-DMSO, δ): 12.63 (1H, broad s), 9.70 (1H, d, J=8 Hz), 8.52 (1H, s), 7.45 (1H, s), 5.83 (1H, dd, J=5, 8 Hz), 5.33 (2H, s), 5.13 (1H, d, J=5 Hz), 4.36 (2H, AB$_q$, J=13 Hz), 3.90 (3H, s), 3.70 (2H, broad s).

(2) 7-[2-Methoxyimino-2-(1,2,3-thiadiazol-4-yl)acetamido]-3-(1-carboxymethyl-1H-tetrazol-5-yl)thiomethyl-3-cephem-4-carboxylic acid (syn isomer).

I.R. (Nujol): 1775, 1720, 1665, 1540 cm$^{-1}$

N.M.R. (d$_6$-DMSO, δ): 9.85 (1H, d, J=8 Hz), 9.40 (1H, s), 5.88 (1H, dd, J=4, 8 Hz), 5.40 (2H, s), 5.17 (1H, d, J=4 Hz), 4.36 (2H, AB$_q$, J=12 Hz), 4.00 (3H, s), 3.70 (2H, AB$_q$, J=16 Hz).

(3) 7-[2-(2-Amino-1,3-thiazol-4-yl)glyoxylamido]-3-(1-carboxymethyl-1H-tetrazol-5-yl)thiomethyl-3-cephem-4-carboxylic acid.

I.R. (Nujol): 1780, 1665, 1520 cm$^{-1}$.

N.M.R. (d$_6$-DMSO, δ): 9.80 (1H, d, J=8 Hz), 7.93 (1H, s), 5.80 (1H, dd, J=5, 8 Hz), 5.37 (2H, s), 5.20 (1H, d, J=5 Hz), 4.40 (2H, AB$_q$, J=13 Hz), 3.73 (2H, broad s).

(4) 7-[2-Methoxyimino-2-(2,3-dihydro-1,4-dithiin-5-yl)-acetamido]-3-(1-carboxymethyl-1H-tetrazol-5-yl)thiomethyl-3-cephem-4-carboxylic acid (syn isomer), pale yellow crystals.

I.R. (Nujol): 3200, 1765, 1730, 1660 cm$^{-1}$.

N.M.R. (d$_6$-DMSO, δ): 9.79 (1H, d, J=8 Hz), 6.65 (1H, s), 5.78 (1H, dd, J=5, 8 Hz), 5.35 (2H, s), 5.15 (1H, d, J=5 Hz), 4.40 (2H, AB$_q$, J=13 Hz), 3.85 (3H, s), 3.73 (2H, broad s), 3.23 (4H, s).

(5) 7-[2-n-Propoxyimino-2-(2-formamido-1,3-thiazol-4-yl)-acetamido-3-(1-carboxymethyl-1H-tetrazol-5-yl)thiomethyl-3-cephem-4-carboxylic acid (syn isomer), white powder.

I.R. (Nujol): 3180, 1770, 1710, 1650 cm$^{-1}$.

N.M.R. (d$_6$-DMSO, δ): 9.57 (1H, d, J=8 Hz), 8.50 (1H, s), 7.35 (1H, s), 5.80 (1H, dd, J=5, 8 Hz), 5.28 (2H, s), 5.10 (1H, d, J=5 Hz), 4.33 (2H, AB$_q$, J=13 Hz), 4.03 (2H, t, J=7 Hz), 3.63 (2H, broad s), 1.67 (2H, m), 0.90 (3H, t, J=7 Hz).

(6) 7-[2-Methoxyimino-2-(3-hydroxyphenyl)acetamido]-3-(1-carboxymethyl-1H-tetrazol-5-yl)thiomethyl-3-cephem-4-carboxylic acid (syn isomer), powder.

I.R. (Nujol): 1767 cm$^{-1}$.

N.M.R. (d$_6$-DMSO, δ): 9.68 (1H, d, J=8 Hz), 6.76~7.36 (4H, m), 5.68 (1H, dd, J=4.2, 8 Hz), 5.06 (1H, d, J=4.2 Hz), 4.66 (2H, s), 4.34 (2H, m), 3.90 (3H, s).

(7) 7-[2-Hydroxyimino-2-(3-hydroxyphenyl)acetamido]-3-(1-carboxymethyl-1H-tetrazol-5-yl)thiomethyl-3-cephem-4-carboxylic acid (syn isomer).

I.R. (Nujol): 3250, 1760, 1660 cm$^{-1}$.

N.M.R. (d$_6$-DMSO, δ): 10.97 (1H, s), 9.60 (1H, d, J=8 Hz), 7.10 (4H, m), 5.87 (1H, dd, J=5, 8 Hz), 5.33 (2H, s), 5.17 (1H, d, J=5 Hz), 4.40 (2H, AB$_q$, J=14 Hz), 3.70 (2H, broad s).

(8) 7-[2-Ethoxyimino-2-(2-formamido-1,3-thiazol-4-yl)-acetamido]-3-(1-carboxymethyl-1H-tetrazol-5-yl)thiomethyl-3-cephem-4-carboxylic acid (syn isomer).

I.R. (Nujol): 3180, 1770, 1710, 1665, 1640 cm$^{-1}$.

N.M.R. (d$_6$-DMSO, δ): 9.87 (1H, d, J=8 Hz), 8.57 (1H, s), 7.43 (1H, s), 5.87 (1H, dd, J=5, 8 Hz), 5.32 (2H, s), 5.18 (1H, d, J=5 Hz), 4.40 (2H, AB$_q$, J=14 Hz), 4.20 (2H, q, J=7 Hz), 3.70 (2H, broad s), 1.27 (3H, t, J=7 Hz).

(9) 7-[2-Ethoxyimino-2-(2-amino-1,3-thiazol-4-yl)acetamido]-3-(1-carboxymethyl-1H-tetrazol-5-yl)thiomethyl-3-cephem-4-carboxylic acid (syn isomer).

I.R. (Nujol): 3280, 1770, 1665 cm$^{-1}$.

N.M.R. (d$_6$-DMSO, δ): 9.60 (1H, d, J=8 Hz), 7.20 (2H, broad s), 6.78 (1H, s), 5.83 (1H, dd, J=5, 8 Hz), 5.33 (2H, s), 5.15 (1H, d, J=8 Hz), 4.35 (2H, AB$_q$, J=14 Hz), 4.15 (2H, t, J=7 Hz), 3.70 (2H, broad s), 1.25 (3H, t, J=7 Hz).

(10) 7-[2-n-Propoxyimino-2-(2-amino-1,3-thiazol-4-yl)-acetamido]-3-(1-carboxymethyl-1H-tetrazol-5-yl)thiomethyl-3-cephem-4-carboxylic acid (syn isomer).

I.R. (Nujol): 3350, 1775, 1660 cm$^{-1}$.

N.M.R. (d$_6$-DMSO, δ): 9.53 (1H, d, J=8 Hz), 7.17 (2H, broad s), 6.70 (1H, s), 5.80 (1H, dd, J=5, 8 Hz), 5.20 (2H, s), 5.10 (1H, d, J=5 Hz), 4.35 (2H, AB$_q$, J=13 Hz), 4.00 (2H, t, J=7 Hz), 3.67 (2H, broad s), 1.63 (2H, m), 0.90 (3H, t, J=7 Hz).

(11) 7-[2-Methoxyimino-2-(3-aminophenyl)acetamido]-3-(1-carboxymethyl-1H-tetrazol-5-yl)thiomethyl-3-cephem-4-carboxylic acid (syn isomer).

I.R. (Nujol): 3600~3100, 1780, 1670, 1650, 1540, 1240, 890, 815 cm$^{-1}$.

N.M.R. (d$_6$-DMSO+D$_2$O, δ): 7.44 (1H, t, J=7 Hz), 6.89 (1H, s), 6.84 (2H, m), 5.82 (1H, d, J=5 Hz), 5.30 (2H, s), 5.12 (1H, d, J=5 Hz), 4.48 (1H, d, J=13 Hz), 4.20 (1H, d, J=13 Hz), 3.90 (3H, s), 3.6 (2H, m).

EXAMPLE 17

(1) The Vilsmeier reagent was prepared from dry dimethylformamide (0.26 ml), phosphorus oxychloride (0.31 ml) and dry ethyl acetate (1 ml) according to a conventional method. Dry methylene chloride (40 ml) and 2-trityloxyimino-2-(2-tritylamino-1,3-thiazol-4-yl)acetic acid (syn isomer) (2.1 g) were added thereto at −3° C., and the resulting mixture was stirred for 30 minutes at the same temperature. The resulting solution was added at −10° C. to a suspension, which was prepared by stirring and warming at 40° C. a mixture of 7-amino-3-(1-carboxymethyl-1H-tetrazol-5-yl)thiomethyl-3-cephem-4-carboxylic acid (1.0 g), dry ethyl acetate (40 ml), trimethylsilylacetamide (2.9 g) and bis(-trimethylsilyl)acetamide (1.7 g), and the resulting mixture was stirred for 2 hours at −10° to −5° C. Water (30 ml) was added to the reaction mixture and the mixture was filtered. To the filtrate was added methylene chloride (20 ml) and the organic layer was separated. To the organic layer was added water (30 ml) and the mixture was adjusted to pH 7.0 with sodium bicarbonate. The aqueous layer was separated, washed with ethyl acetate and, after addition of ethyl acetate (100 ml), adjusted to pH 3.0 under stirring with conc. hydrochloric acid. The ethyl acetate layer was separated, washed with water, dried over magnesium sulfate and concentrated to dryness to give 7-[2-trityloxyimino-2-(2-tritylamino-1,3-thiazol-4-yl)acetamido]-3-(1-carboxymethyl-1H-tetrazol-5-yl)thiomethyl-3-cephem-4-carboxylic acid (syn isomer) (0.48 g).

(2) This compound (0.48 g) was suspended in tetrahydrofuran (10 ml) and 50% aqueous solution of formic acid (3.8 ml) was added thereto. The resulting mixture was stirred for 2 hours at 55° C. The reaction mixture was filtered, and the filtrate was concentrated to dryness to give 7-[2-hydroxyimino-2-(2-amino-1,3-thiazol-4-yl)acetamido]-3-(1-carboxymethyl-1H-tetrazol-5-yl)thiomethyl-3-cephem-4-carboxylic acid (syn isomer) (0.13 g).

IR (Nujol): 1760, 1655, 1620 cm$^{-1}$.

NMR (d$_6$-DMSO, δ): 9.48 (1H, d, J=8 Hz), 6.66 (1H, s), 5.80 (1H, dd, J=5, 8 Hz), 5.15 (2H, s), 5.00 (1H, d, J=5 Hz), 4.32 (2H, m), 3.65 (2H, m).

EXAMPLE 18

The following compounds were obtained according to similar manners to those of the above Examples.

(1) 7-[2-Allyloxyimino-2-(2-formamido-1,3-thiazol-4-yl)acetamido]-3-(1-carboxymethyl-1H-tetrazol-5-yl)thiomethyl-3-cephem-4-carboxylic acid (syn isomer).

IR (Nujol): 3210, 1775, 1675 cm$^{-1}$.

NMR (d$_6$-DMSO, δ): 9.72 (1H, d, J=8 Hz), 8.51 (1H, s), 7.42 (1H, s), 5.75-6.25 (1H, m), 5.83 (1H, dd, J=5, 8 Hz), 5.0-5.48 (2H, m), 5.29 (2H, s), 5.15 (1H, d, J=5 Hz), 4.65 (2H, d, J=6 Hz), 4.35 (2H, AB$_q$, J=14 Hz), 3.68 (2H, AB$_q$, J=18.5 Hz).

(2) 7-[2-Allyloxyimino-2-(2-amino-1,3-thiazol-4-yl)acetamido]-3-(1-carboxymethyl-1H-tetrazol-5-yl)thiomethyl-3-cephem-4-carboxylic acid hydrochloride (syn isomer).

IR (Nujol): 3300, 3200, 1770, 1730, 1660, 1640 cm$^{-1}$.

NMR (d$_6$-DMSO, δ): 9.90 (1H, d, J=8 Hz), 6.99 (1H, s), 5.70-6.30 (1H, m), 5.80 (1H, dd, J=5, 8 Hz), 5.31 (2H, s), 5.00-5.58 (3H, m), 4.71 (2H, d, J=4 Hz), 4.38 (2H, ABq, J=15 Hz), 3.73 (2H, ABq, J=18 Hz).

(3) 7-[2-Hydroxyimino-2-(2-amino-1,3-thiazol-4-yl)acetamido]-3-(1-carboxymethyl-1H-tetrazol-5-yl)thiomethyl-3-cephem-4-carboxylic acid (syn isomer).

IR (Nujol): 1760, 1655, 1620 cm$^{-1}$.

NMR (d$_6$-DMSO, δ): 9.48 (1H, d, J=8.0 Hz), 6.66 (1H, s), 5.80 (1H, dd, J=5, 8 Hz), 5.15 (2H, s), 5.00 (1H, d, J=5 Hz), 4.32 (2H, m), 3.65 (2H, m).

(4) 7-[2-(2-Propynyl)oxyimino-2-(2-formamido-1,3-thiazol-4-yl)acetamido]-3-(1-carboxymethyl-1H-tetrazol-5-yl)thiomethyl-3-cephem-4-carboxylic acid (syn isomer).

IR (Nujol): 3250, 1770, 1670 cm$^{-1}$.

NMR (d$_6$-DMSO, δ): 3.49 (1H, m), 3.70 (2H, m), 4.37 (2H, m), 4.82 (2H, m), 5.18 (1H, d, J=5.0 Hz), 5.23 (2H, s), 5.86 (1H, dd, J=5.0 and 8.0 Hz), 7.53 (1H, s), 8.65 (1H, s), 9.90 (1H, d, J=8.0 Hz).

(5) 7-[2-(2-Propynyl)oxyimino-2-(2-amino-1,3-thiazol-4-yl)-acetamido]-3-(1-carboxymethyl-1H-tetrazol-5-yl)thiomethyl-3-cephem-4-carboxylic acid (syn isomer).

IR (Nujol): 3280, 1770, 1660, 1635 cm$^{-1}$.

NMR (d$_6$-DMSO, δ): 3.41 (1H, m), 3.64 (2H, m), 4.32 (2H, AB q, J=12.0 Hz), 4.67 (2H, m), 5.08 (1H, d, J=4.0 Hz), 5.26 (2H, s), 5.74 (1H, d d, J=4.0 and 8.0 Hz), 6.75 (1H, s), 7.20 (2H, broad s), 9.64 (1H, d, J=8.0 Hz).

(6) 7-[2-Hexyloxyimino-2-(2-formamido-1,3-thiazol-4-yl)acetamido]3-(1-carboxymethyl-1H-tetrazol-5-yl)thiomethyl-3-cephem-4-carboxylic acid (syn isomer).

(7) 7-[2-Hexyloxyimino-2-(2-amino-1,3-thiazol-4-yl)acetamido]-3-(1-carboxymethyl-1H-tetrazol-5-yl)thiomethyl-3-cephem-4-carboxylic acid (syn isomer).

(8) 7-[2-Isopropoxyimino-2-(2-amino-1,3-thiazol-4-yl)acetamido]3-(1-carboxymethyl-1H-tetrazol-5-yl)thiomethyl-3-cephem-4-carboxylic acid (syn isomer).

IR (Nujol): 3300, 1760, 1700, 1650 cm$^{-1}$.

NMR (d$_6$-DMSO, δ): 1.25 (6H, d, J=6.0 Hz), 3.69 (2H, ABq, J=18.0 Hz), 3.86-4.69 (3H, m), 5.13 (1H, d, J=5.0 Hz), 5.31 (2H, s), 5.81 (1H, d d, J=5.0 and 8.0 Hz), 6.75 (1H, s), 9.56 (1H, d, J=8.0 Hz).

EXAMPLE 19

Phosphorus oxychloride (0.8 g) was added at 0° C. to a mixture of 2-benzyloxyimino-2-(2-aminothiazol4-yl)acetic acid (syn isomer) (1.1 g) and dry tetrahydrofuran (11.0 ml), and the mixture was stirred for 15 minutes at 0° C. Trimethylsilylacetamide (0.7 g) was added thereto and it was stirred for 15 minutes. Phosphorus oxychloride (0.8 g) was added thereto and it was stirred for 15 minutes. To the resulting mixture was added dry dimethylformamide (0.4 g) and it was stirred for 30 minutes at 0°-3° C. to give clear solution.

On the other hand, acetone (9.0 ml) was added to a solution of 7-amino-3-(1-carboxymethyl-1H-tetrazol-5-yl)thiomethyl-3-cephem-4-carboxylic acid (1.5 g) and sodium bicarbonate (1.0 g) in water (9.0 ml) and thereto was added the clear solution as obtained above at −3° to 3° C. and pH 7.5 to 8.5. The mixture was stirred for 1 hour at the same temperature and pH. An aqueous layer was separated and washed with ethyl acetate. After distilling off the remaining ethyl acetate, the aqueous layer was adjusted to pH 5.0 with 10% hydrochloric acid and subjected to column chromatography on Diaion HP-20 resin (Trademark: prepared by Mitsubishi Chemical Industries Ltd.) using 10% isopropyl alcohol as an eluent. The eluate was adjusted to pH 2.7 with 10% hydrochloric acid and precipitates were collected by filtration, washed with water and dried to give 7-[2-benzyloxyimino-2-(2-aminothiazol-4-yl)acetamido]-3-(1-carboxymethyl-1H-tetrazol-5-yl)thiomethyl-3-cephem-4-carboxylic acid (syn isomer)(0.78 g).

I.R. (Nujol): 3250, 1760, 1650 cm$^{-1}$.

N.M.R. (DMSO-d$_6$, δ): 3.65 (2H, ABq, J=18 Hz), 4.37 (2H, ABq, J=14 Hz), 5.09 (1H,d,J=4 Hz), 5.19 (2H, s), 5.33 (2H, s), 5.80 (1H, d d, J=4 and 8 Hz), 6.81 (1H, s), 7.40 (5H, m), 9.76 (1H, d, J=8 Hz).

EXAMPLE 20

(1) 2-(2-Propynyloxyimino)-2-(2-aminothiazol-4-yl)-acetic acid (syn isomer)(10.0 g) and 2,2,2-trifluoroacetic anhydride (22.5 g) were reacted in the presence of bis(-trimethylsilyl)acetamide (22.3 g) and dry ethyl acetate (100 ml) to give 2-(2-propynyloxyimino)-2-[2-(2,2,2-trifluoroacetamido)thiazol-4-yl]acetic acid (syn isomer)(11.4 g).

I.R. (Nujol): 3280, 3130, 2140, 1710, 1575, 1360, 1260, 1210, 1165, 1075, 1020, 980, 750 cm$^{-1}$.

N.M.R. (DMSO-d$_6$,δ): 3.53 (1H, t, J=2 Hz), 4.83 (2H, d, J=2 Hz), 7.73 (1H, s).

(2) 7-aminocephalosporanic acid (38.4 g) and 1-(2-carboxyethyl)-1H-tetrazole-5-thiol (20.0 g) were reacted in the presence of boron trifluoride etherate (80.0 g) and dry acetonitrile (200 ml) to give 7-amino-3-[1-(2-carboxyethyl)-1H-tetrazol-5-yl]thiomethyl-3-cephem-4-carboxylic acid (35.52 g).

I.R. (Nujol): 1800, 1720, 1620, 1540, 1410, 1345 cm$^{-1}$.

N.M.R. (DMSO-d$_6$,δ): 2.93 (2H, t, J=6 Hz), 3.67 (2H, m), 4.37-4.57 (4H, m), 4.73-5.03 (2H, m).

(3) 7-Amino-3-[1-(2-carboxyethyl)-1H-tetrazol-5-yl]thiomethyl-3-cephem-4-carboxylic acid (1.93 g) and 2-(2-propynyloxyimino)-2-[2-(2,2,2-trifluoroacetamido)thiazol-4-yl]acetic acid (syn isomer) (1.61 g) were reacted in the presence of Vilsmeier reagent prepared from dimethylformamide and phosphorus oxychloride to give 7-[2-(2-propynyloxyimino)-2-{2-(2,2,2-trifluoroacetamido)thiazol-4-yl}acetamido]-3-[1-(2-carboxyethyl)-1H-tetrazol-5-yl]thiomethyl-3-cephem-4-carboxylic acid (syn isomer)(3.0 g).

I.R. (Nujol): 2120, 1770, 1720, 1670, 1560, 1260, 1210, 1160, 1030, 1010 cm$^{-1}$.

N.M.R. (DMSO-d$_6$,δ): 3.03 (2H, t, J=7 Hz), 3.47 (1H, m), 3.70 (2H, m), 4.33-4.53 (4H, m), 4.73 (2H, m), 5.10 (1H, d, J=5 Hz), 5.77 (1H, dd, J=5 and 8 Hz), 7.33 (1H, s), 9.70 (1H, d, J=8 Hz).

EXAMPLE 21

The following compounds were obtained according to similar manners to those of Examples 19 and 20.

(1) 7-[2-Isopropoxyimino-2-{2-(2,2,2-trifluoroacetamido)thiazol-4-yl}-acetamido]-3-[1-(2-carboxyethyl)-1H-tetrazol-5-yl]thiomethyl-3-cephem4-carboxylic acid (syn isomer).

I.R. (Nujol): 1770, 1720, 1660, 1260, 1210, 1170 cm$^{-1}$.

N.M.R. (DMSO-d$_6$,δ): 1.27 (6H, d, J=7 Hz), 3.03 (2H, t, J=6 Hz), 3.73 (2H, m), 4.33-4.63 (5H, m), 5.15 (1H, d, J=5 Hz), 5.80 (1H, m), 7.43 (1H, s), 9.70 (1H, d, J=8 Hz).

(2) 7-[2-Allyloxyimino-2-(2-formamidothiazol-4-yl)acetamido]-3-[1-(2-carboxyethyl)-1H-tetrazol-5-yl]thiomethyl-3-cephem-4-carboxylic acid (syn isomer).

I.R. (Nujol): 1770, 1670, 1550 cm$^{-1}$.

N.M.R. (DMSO-d$_6$,δ): 2.97 (2H, t, J=6 Hz), 3.73 (2H, m), 4.37-4.73 (6H, m), 5.20 (1H, d, J=5 Hz), 5.40 (2H, dd, J=2 and 11 Hz), 5.77-6.00 (2H, m), 7.47 (1H, s), 8.57 (1H, s), 9.75 (1H, d, J=8 Hz), 12.70 (1H, broad s)

(3) 7-[2-(p-Tolylmethoxyimino)-2-{2-(2,2,2-trifluoroacetamido)thiazol-4-yl}acetamido]-3-(1-carboxymethyl-1H-tetrazol-5-yl)thiomethyl-3-cephem-4-carboxylic acid (syn isomer).

I.R. (Nujol): 1770, 1660-1620, 1250, 1000 cm$^{-1}$.

N.M.R. (DMSO-d$_6$,δ): 2.30 (3H, s), 3.67 (2H, m), 4.37 (2H, m), 5.13 (3H, m), 5.33 (2H, s), 7.23 (4H, m), 7.53 (1H, s), 9.80 (1H, d, J=8 Hz).

(4) 7-[2-(p-Tolylmethoxyimino)-2-(2-aminothiazol-4-yl)acetamido]-3-(1-carboxymethyl-1H-tetrazol-5-yl)thiomethyl-3-cephem-4-carboxylic acid (syn isomer).

I.R. (Nujol): 3400, 3300, 1770, 1710, 1640, 1530, 1440, 1370, 1360, 1250, 1010 cm$^{-1}$.

(5) 7-[2-methoxyimino-2-(2-aminothiazol-4-yl)acetamido]-3-(1-methoxycarbonylmethyl-1H-tetrazol-5-yl)thiomethyl-3-cephem-4-carboxylic acid (syn isomer).

I.R. (Nujol): 3300, 3200, 1765, 1660, 1630 cm$^{-1}$.

(6) 7-[2-Methoxyimino-2-(2-formamidothiazol-4-yl)acetamido]-3-(1-methoxycarbonylmethyl-1H-tetrazol-5-yl)thiomethyl-3-cephem-4-carboxylic acid (syn isomer).

I.R. (Nujol): 3300, 1780, 1750, 1670 cm$^{-1}$.

N.M.R. (DMSO-d$_6$,δ): 3.72 (2H, m), 3.78 (3H, s), 3.93 (3H, s), 4.38 (2H, ABq, J=14 Hz), 5.16 (1H, d, J=5 Hz), 5.48 (2H, s), 5.84 (1H, dd, J=5 and 8 Hz), 7.44 (1H, s), 8.54 (1H, s), 9.68 (1H, d, J=8 Hz), 12.70 (1H, broad s).

(7) 7-[2-(2-Propynyloxyimino)-2-(2-aminothiazol-4-yl)acetamido]-3-(1-methoxycarbonylmethyl-1H-tetrazol-5-yl)thiomethyl-3-cephem-4-carboxylic acid (syn isomer).

I.R. (Nujol): 3320, 2150, 1780, 1760, 1680, 1630 cm$^{-1}$.

N.M.R. (DMSO-d$_6$,δ): 3.47 (1H, m), 3.71 (2H, m), 3.79 (3H, s), 4.38 (2H, ABq, J=14 Hz), 4.73 (2H, m), 5.16 (1H, d, J=5Hz), 5.49 (2H, s), 5.81 (1H, dd, J=5 and 8 Hz), 6.82 (1H, s), 7.26 (2H, broad s), 9.69 (1H, d, J=8 Hz).

(8) 7-[2-Propynyloxyimino)-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3260, 2110, 1765, 1660, 1475 cm$^{-1}$.

(9) 7-[2-Allyloxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 1770, 1660, 1530 cm$^{-1}$.

(10) 7-[2-Isopropoxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3400, 3260, 1770, 1650, 1610, 1530 cm$^{-1}$.

(11) 7-[2-Cyclopentyloxyimino-2-(2-formamidothiazol-4-yl)acetamido]-3-(1-carboxymethyl-1H-tetrazol-5-yl)thiomethyl-3-cephem-4-carboxylic acid (syn isomer).

I.R. (Nujol): 3200, 1770, 1670, 1540 cm$^{-1}$.

N.M.R. (DMSO-d$_6$,δ): 1.3-2.1 (8H, m), 3.69 (2H, broad s), 4.38 (2H, ABq, J=14 Hz), 4.7 (1H, broad s), 5.13 (1H, d, J=5 Hz), 5.32 (2H, s), 5.84 (1H, dd, J=5 and 8 Hz), 7.40 (1H, s), 8.55 (1H, s), 9.65 (1H, d, J=8 Hz), 12.74 (1H, broad s).

(12) 7-[2-Cyclopentyloxyimino-2-(2-aminothiazol-4-yl)acetamido]-3-(1-carboxymethyl-1H-tetrazol-5-yl)thiomethyl-3-cephem-4-carboxylic acid (syn isomer).

I.R. (Nujol): 3260, 1765, 1650, 1620, 1530 cm$^{-1}$.

(13) 7-[2-Cyclopentyloxyimino-2-{2-(2,2,2-trifluoroacetamido)thiazol-4-yl}acetamido]-3-[1-(2-carboxyethyl)-1H-tetrazol-5-yl]thiomethyl-3-cephem-4-carboxylic acid (syn isomer).

I.R. (Nujol): 1770, 1710, 1640 cm$^{-1}$.

(14) 7-[2-Cyclopentyloxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3300, 3200, 1770, 1650 cm$^{-1}$.

EXAMPLE 22

A solution of sodium acetate trihydrate (5.97 g) in water (25 ml) was added to 7-[2-(2-propynyloxyimino)-2-{2-(2,2,2-trifluoroacetamido)thiazol-4-yl}acetamido]-3-[1-(2-carboxyethyl)-1H-tetrazol-5-yl]thiomethyl-3-cephem-4-carboxylic acid (syn isomer)(3.0 g) and the mixture was stirred overnight. The reaction mixture was adjusted to pH 3 with 10% hydrochloric acid under ice-cooling and precipitates were collected by filtration, washed with water and dried to give 7-[2-propynyloxyimino)-2-(2-aminothiazol-4-yl)acetamido]-3-[1-(2-carboxyethyl)-1H-tetrazol-5-yl]thiomethyl-3-cephem-4-carboxylic acid (syn isomer) (1.80 g).

I.R. (Nujol): 3260, 2110, 1765, 1660, 1475 cm$^{-1}$.

N.M.R. (DMSO-d$_6$,δ): 2.92 (2H, t, J=6 Hz), 3.42 (1H, m), 3.67 (2H, m), 4.30-4.53 (4H, m), 4.70 (2H, m), 5.10 (1H, d, J=5 Hz), 5.73 (1H, dd, J=5 and 8 Hz), 6.73 (1H, s), 7.20 (2H, broad s), 9.58 (1H, d, J=8 Hz).

EXAMPLE 23

Conc. hydrochloric acid (572 mg) was added to a solution of 7-[2-allyloxyimino-2-(2-formamidothiazol-4-yl)acetamido]-3-[1-(2-carboxyethyl)-1H-tetrazol-5-yl]thiomethyl-3-cephem-4-carboxylic acid (syn isomer) (2.28 g) in methanol (16 ml) at ambient temperature and the mixture was stirred for 30 minutes. The reaction mixture was post-treated according to a conventional manner to give 7-[2-allyloxyimino-2-(2-aminothiazol-4-yl)acetamido]-3-[1-(2-carboxyethyl)-1H-tetrazol-5-yl]thiomethyl-3-cephem-4-carboxylic acid (syn isomer)(410 mg).

I.R. (Nujol): 1770, 1660, 1530 cm$^{-1}$.

N.M.R. (DMSO-d$_6$,δ): 2.90 (2H, t, J=7 Hz), 3.67 (2H, broad s), 4.30-4.63 (6H, m), 5.10 (1H, d, J=5 Hz), 5.33 (2H, dd, J=2 and 12 Hz), 5.67-6.07 (2H, m), 6.73 (1H, s), 7.20 (3H, broad s), 9.63 (1H, d, J=8 Hz).

EXAMPLE 24

The following compounds were obtained according to similar manners to those of Example 22 and 23.

(1) 7-[2-Benzyloxyimino-2-(2-aminothiazol-4-yl)acetamido]-3-(1-carboxymethyl-1H-tetrazol-5-yl)thiomethyl-3-cephem-4-carboxylic acid (syn isomer).

I.R. (Nujol): 3250, 1760, 1650 cm$^{-1}$.

(2) 7-[2-(p-Tolylmethoxyimino)-2-(2-aminothiazol-4-yl)acetamido]-3-(1-carboxymethyl-1H-tetrazol-5-yl)thiomethyl-3-cephem-4-carboxylic acid (syn isomer).

I.R. (Nujol): 3400, 3300, 1770, 1710, 1640, 1530, 1440, 1370, 1360, 1250, 1010 cm$^{-1}$.

N.M.R. (DMSO-d$_6$,δ): 2.27 (3H, s), 3.60 (2H, m), 4.33 (2H, ABq, J=14 Hz), 5.07 (2H, s), 5.10 (1H, d, J=6 Hz), 5.77 (1H,dd, J=6 and 8 Hz), 6.70 (1H,s), 7.20 (4H,m), 9.66 (1H,d,J=8 Hz).

(3) 7-[2-Methoxyimino-2-(2-aminothiazol-4-yl)acetamido]3-(1-methoxycarbonylmethyl-1H-tetrazol-5-yl)thiomethyl3-cephem-4-carboxylic acid (syn isomer).

I.R. (Nujol): 3300, 3200, 1765, 1660, 1630 cm$^{-1}$.

N.M.R. (DMSO-d$_6$,δ): 3.73 (2H, m), 3.79 (3H, s), 3.91 (3H, s), 4.30 (2H, ABq, J=14 Hz), 5.15 (1H,d, J=4 Hz), 5.50 (2H, s), 5.81 (1H, dd, J=4 and 8 Hz), 6.81 (1H, s), 9.65 (1H, d, J=8 Hz).

(4) 7-[2-(2-Propynyloxyimino)-2-(2-aminothiazol-4-yl)acetamido]-3-(1-methoxycarbonylmethyl-1H-tetrazol-5-yl)thiomethyl-3-cephem-4-carboxylic acid (syn isomer).

I.R. (Nujol): 3320, 2150, 1780, 1760, 1680, 1630 cm$^{-1}$.

(5) 7-[2-Isopropoxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3400, 3260, 1770, 1650, 1610, 1530 cm$^{-1}$.

N.M.R. (DMSO-d$_6$,δ): 1.23 (2H, d, J=6 Hz), 2.93 (2H, t, J=6 Hz), 3.70 (2H, m), 4.20–4.53 (5H, m), 5.10 (1H, d, J=5 Hz), 5.77 (1H, dd, J=5 and 8 Hz), 6.67 (1H, s), 7.17 (2H, broad s), 9.77 (1H, d, J=8 Hz).

(6) 7-[2-Cyclopentyloxyimino-2-(2-aminothiazol-4-yl)acetamido]-3-(1-carboxymethyl-1H-tetrazol-5-yl)thiomethyl-3-cephem-4-carboxylic acid (syn isomer).

I.R. (Nujol): 3260, 1765, 1650, 1620, 1530 cm$^{-1}$.

N.M.R. (DMSO-d$_6$,δ): 1.2–2.2 (8H, m), 3.74 (2H, broad s), 4.40 (2H, ABq, J=14 Hz), 4.68 (1H, m), 5.17 (1H, d, J=5 Hz), 5.33 (2H, s), 5.85 (1H, dd, J=5 and 8 Hz), 6.78 (1H, s), 7.32 (2H, broad s), 9.66 (1H, d, J=8 Hz).

(7) 7-[2-Cyclopentyloxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3300, 3200, 1770, 1650 cm$^{-1}$.

N.M.R. (DMSO-d$_6$,δ): 1.33–2.13 (8H, m), 2.94 (2H, t, J=6 Hz), 3.71 (2H, m), 4.04–4.87 (4H, m), 5.13 (1H, d, J=5 Hz), 5.77 (1H, dd, J=5 and 8 Hz), 6.70 (1H, s), 9.47 (1H, d, J=8 Hz).

Preparation 1

(1) 1-Carboxymethyl-1H-tetrazole-5-thiol and methanol were reacted in the presence of conc.sulfuric acid to give 1-methoxycarbonylmethyl-1H-tetrazole-5-thiol.

I.R. (Nujol): 3100, 1735 cm$^{-1}$.

N.M.R. (DMSO-d$_6$,δ): 3.72 (3H, s), 5.20 (2H, s), 14.30 (1H, broad s).

(2) 7-Aminocephalosporanic acid was reacted with 1-methoxycarbonylmethyl-1H-tetrazole-5-thiol in a conventional manner to give 7-amino-3-(1-methoxycarbonylmethyl-1H-tetrazol-5-yl)thiomethyl-3-cephem-4-carboxylic acid.

N.M.R. (DMSO-d$_6$, δ): 3.67 (2H, m), 3.74 (3H, s), 4.34 (2H, ABq, J=14 Hz), 4.78 (1H, d, J=5 Hz), 4.97 (1H, d, J=5 Hz), 5.45 (2H, s).

Preparation 2

2-Isopropoxyimino-2-(2-aminothiazol-4-yl)acetic acid (syn isomer) (15.0 g) was reacted with 2,2,2-trifluoroacetic anhydride according to a similar manner to that of Example 20 (1) to give 2-isopropoxyimino-2-[2-(2,2,2-trifluoroacetamido)thiazol-4-yl]acetic acid (syn isomer).

I.R. (Nujol): 1720, 1580, 1260, 1210, 1150, 1000 cm$^{-1}$.

N.M.R. (DMSO-d$_6$, δ): 1.30 (6H, d, J=6 Hz), 4.47 (1H, quintet, J=6 Hz), 7.70 (1H, s).

What we claim is:
1. 3,7-Disubstituted-3-cephem-4-carboxylic acid compounds of the formula:

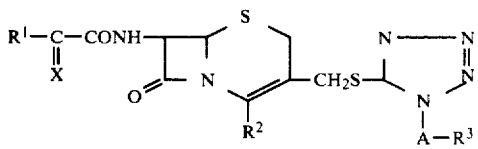

wherein $R^1$ is 2-amino-, lower alkanoylamino- or halo(lower)alkanoylamino substituted thiazol-4-yl;

$R^2$ and $R^3$ are each carboxy or an esterified carboxy;

X is lower alkynyloxyimino; and

A is lower alkylene, and pharmaceutically acceptable salt thereof.

2. Syn isomer of the compound of claim 1.

3. The compound of claim 2, wherein $R^2$ is carboxy, and $R^3$ is carboxy or lower alkoxycarbonyl.

4. The compound of claim 3, wherein $R^1$ is 2-amino-, formamido- or 2,2,2-trifluoroacetamido substituted thiazol-4-yl;

$R^3$ is carboxy or methoxycarbonyl;

X is 2-propynyloxyimino, and

A is methylene or ethylene.

5. The compound of claim 4, which is 7-[2-(2-propynyloxyimino)-2-(2-aminothiazol-4-yl)acetamido]-3-(1-carboxymethyl-1H-tetrazol-5-yl)thiomethyl-3-cephem-4-carboxylic acid (syn isomer).

6. The compound of claim 4, which is 7-[2-(2-propynyloxyimino)-2-(2-aminothiazol-4-yl)acetamido]-3-[1-(2-carboxyethyl)-1H-tetrazol-5-yl]thiomethyl-3-cephem-4-carboxylic acid (syn isomer).

7. A pharmaceutical antibacterial composition comprising a compound of claim 1 in association with a pharmaceutically acceptable, substantially non-toxic carrier or excipient.

* * * * *